US009550873B2

(12) United States Patent
Park et al.

(10) Patent No.: US 9,550,873 B2
(45) Date of Patent: Jan. 24, 2017

(54) DOPED CHIRAL POLYMER METAMATERIALS

(71) Applicants: National Institute of Aerospace, Hampton, VA (US); The United States of America as represented by the Administrator of the National Aeronautics and Space Administration, Washington, DC (US)

(72) Inventors: Cheol Park, Yorktown, VA (US); Jin Ho Kang, Newport News, VA (US); Keith L. Gordon, Hampton, VA (US); Godfrey Sauti, Hampton, VA (US); Sharon E. Lowther, Hampton, VA (US); Robert G. Bryant, Poquoson, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 606 days.

(21) Appl. No.: 13/941,441

(22) Filed: Jul. 12, 2013

(65) Prior Publication Data
US 2014/0017480 A1 Jan. 16, 2014

Related U.S. Application Data

(60) Provisional application No. 61/671,217, filed on Jul. 13, 2012.

(51) Int. Cl.
| | | |
|---|---|---|
| C08K 3/04 | (2006.01) |
| C07K 14/00 | (2006.01) |
| C08K 3/08 | (2006.01) |
| C08K 3/24 | (2006.01) |
| C08K 3/28 | (2006.01) |
| C08K 3/30 | (2006.01) |
| C08K 3/32 | (2006.01) |
| C08K 3/38 | (2006.01) |
| C08K 5/3445 | (2006.01) |
| C08K 5/42 | (2006.01) |
| C08L 49/00 | (2006.01) |
| C08L 67/00 | (2006.01) |
| C08L 67/04 | (2006.01) |
| G02B 1/00 | (2006.01) |
| H01Q 15/00 | (2006.01) |
| G02F 1/29 | (2006.01) |

(52) U.S. Cl.
CPC ............... *C08K 3/04* (2013.01); *C07K 14/001* (2013.01); *C08K 3/08* (2013.01); *C08K 3/24* (2013.01); *C08K 3/28* (2013.01); *C08K 3/30* (2013.01); *C08K 3/32* (2013.01); *C08K 3/38* (2013.01); *C08K 5/3445* (2013.01); *C08K 5/42* (2013.01); *C08L 49/00* (2013.01); *C08L 67/00* (2013.01); *C08L 67/04* (2013.01); *G02B 1/002* (2013.01); *H01Q 15/0086* (2013.01); *G02F 1/29* (2013.01); *G02F 2202/30* (2013.01); *Y10T 428/249921* (2015.04)

(58) Field of Classification Search
CPC ............... C08K 3/04; C08K 3/08; C08K 3/28; C08K 3/32; C08K 3/38; C08K 5/3445; C08K 5/42; C07K 14/001; C08L 49/00; C08L 67/00; C08L 67/04; G02B 1/002; H01Q 15/249921; Y10T 428/24921; G02F 1/29; G02F 2202/30
See application file for complete search history.

(56) References Cited

U.S. PATENT DOCUMENTS

| | | |
|---|---|---|
| 2007/0120114 A1 | 5/2007 | Wang et al. |
| 2008/0089645 A1 | 4/2008 | Wang et al. |
| 2010/0086750 A1* | 4/2010 | Blumberg et al. ...... B32B 27/00 428/195.1 |
| 2011/0068291 A1 | 3/2011 | Park et al. |
| 2011/0085229 A1* | 4/2011 | Lavrentovich et al. ... G02F 1/29 359/315 |

FOREIGN PATENT DOCUMENTS

| | | |
|---|---|---|
| WO | 90/03102 | 3/1990 |
| WO | 96/26385 | 8/1996 |

OTHER PUBLICATIONS

Lagarkov et al.; "Electrophysics and Electrodynamics of Metamaterials"; High Temperature, Kluwer Academic Publishers-Plenum Publishers, NE; vol. 48, No. 6; Dec. 29, 2010; pp. 983-999, XP019855357, DOI: 10.1134/S0018151X10060258.

* cited by examiner

*Primary Examiner* — Nathan M Nutter
(74) *Attorney, Agent, or Firm* — Thomas K. McBride; Robin W. Edwards; Jennifer L. Riley

(57) ABSTRACT

Some implementations provide a composite material that includes a first material and a second material. In some implementations, the composite material is a metamaterial. The first material includes a chiral polymer (e.g., crystalline chiral helical polymer, poly-γ-benzyl-L-glutamate (PBLG), poly-L-lactic acid (PLA), polypeptide, and/or polyacetylene). The second material is within the chiral polymer. The first material and the second material are configured to provide an effective index of refraction value for the composite material of 1 or less. In some implementations, the effective index of refraction value for the composite material is negative. In some implementations, the effective index of refraction value for the composite material of 1 or less is at least in a wavelength of one of at least a visible spectrum, an infrared spectrum, a microwave spectrum, and/or an ultraviolet spectrum.

42 Claims, 21 Drawing Sheets

Direct Mixing

Super Critical Fluid (SCF) Infusion

Super Critical Fluid (SCF) Infusion

Super Critical Fluid (SCF) Infusion

Super Critical Fluid (SCF) Infusion

Single wall carbon nanotube in polymer

Silver (Ag) - poly-γ-benzyl-L-glutamate (PBLG) Composite Film

DOPED CHIRAL POLYMER METAMATERIALS

CROSS REFERENCE TO RELATED APPLICATION

The present application claims priority to U.S. Provisional Application No. 61/671,217 titled "Dope Chiral Polymer Negative Index Materials (DCPNIM)", filed Jul. 13, 2012, which is hereby expressly incorporated by reference herein

STATEMENT REGARDING FEDERALLY SPONSORED RESEARCH

The invention described herein was made in the performance of work under a NASA cooperative agreement and by employees of the United States Government and is subject to the provisions of Public Law 96-517 (35 U.S.C. §202) and may be manufactured and used by or for the Government for governmental purposes without the payment of any royalties thereon or therefore. In accordance with 35 U.S.C. §202, the cooperative agreement recipient elected to retain title.

BACKGROUND

Field

Various features relate to doped chiral polymer metamaterials.

Background

A metamaterial is a man-made material that exhibits particular properties and/or behaviors that cannot be found in natural occurring material. Typically, metamaterials are engineered to achieve particular objectives. Metamaterials are assembled from several discrete individual elements made of microscopic materials, such as metals and plastics. These materials are arranged together in a periodic pattern structure and/or repeating design structure. It is this periodic pattern structure and/or repeating design structure that provide metamaterials with their unique properties and/or behaviors.

FIG. 1 illustrates an example of a metamaterial 100. As shown in FIG. 1, the metamaterial includes a set of repeating structures 102. Each repeating structure 102 includes several discrete elements. Specifically, each repeating structure 102 includes a board 104, a first split-ring resonator 106, a second split-ring resonator 108, a third split-ring resonator 110, and a wire 112. Each repeating structure 102 is arranged in a periodic repeating pattern to form the metamaterial 100. For example a first repeating structure 102 is positioned parallel to a second repeating structure 120. In addition, a third repeating structure 130 is positioned orthogonally to the first repeating structure 120 and/or the second repeating structure 130.

One major downside to current metamaterials is that they are difficult to manufacture due to the complexity of their structure. This limits their use in greater wavelength ranges than the complex repeating unit size, not readily available for optical ranges. In addition, the way the repeating structures are coupled together in the metamaterials makes them extremely rigid and unflexible.

Therefore, there is a need for material that exhibits exotic electromagnetic properties and/or behaviors without complex repeating architectures and geometries. Ideally, such a composite material will be easy to manufacture, void of some of the structural complexities of current metamaterials, can be manufactured at lower cost than that current metamaterials, and/or exhibits more flexibility than current metamaterials.

DRAWINGS

Various features and advantages may become apparent from the detailed description set forth below when taken in conjunction with the drawings in which like reference characters identify correspondingly throughout.

Figure 16A:
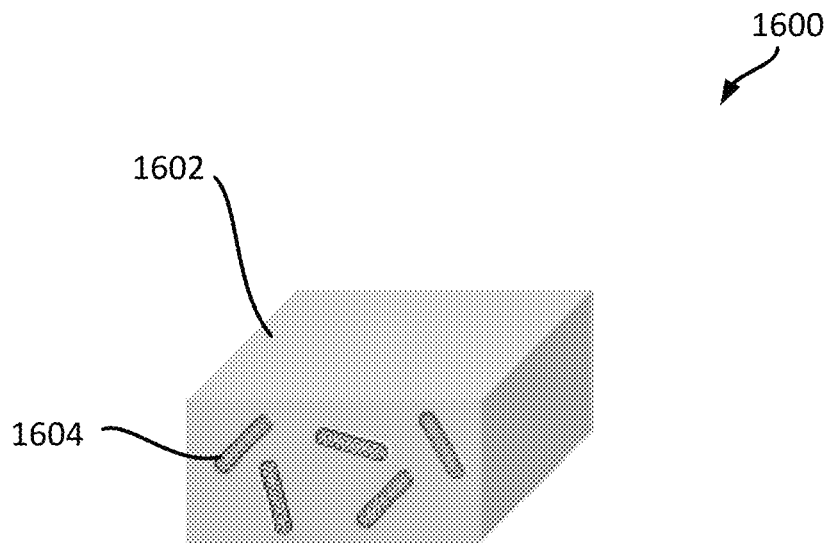

FIG. 16A composite material that includes nanoinclusion before tuning the index of refraction using an electric field.

Figure 16B:
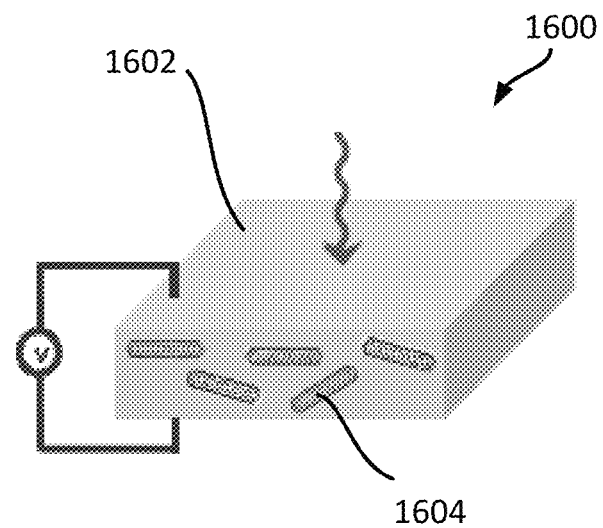

FIG. 16B composite material that includes nanoinclusion with a tuned index of refraction using an electric field.

Figure 17:
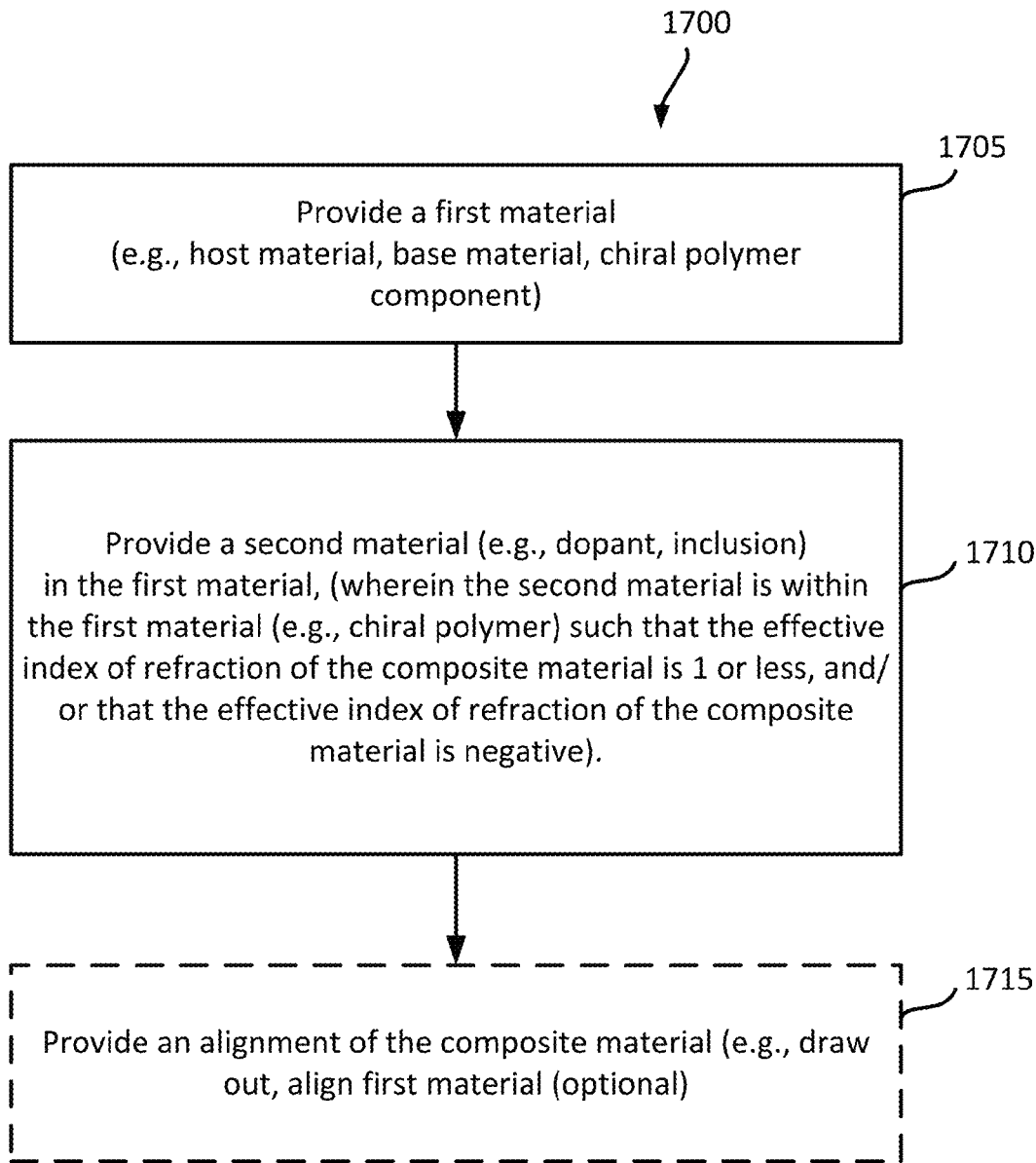

FIG. 17 illustrates a method for providing/manufacturing a composite material that includes drawing the composite material.

Figure 18:
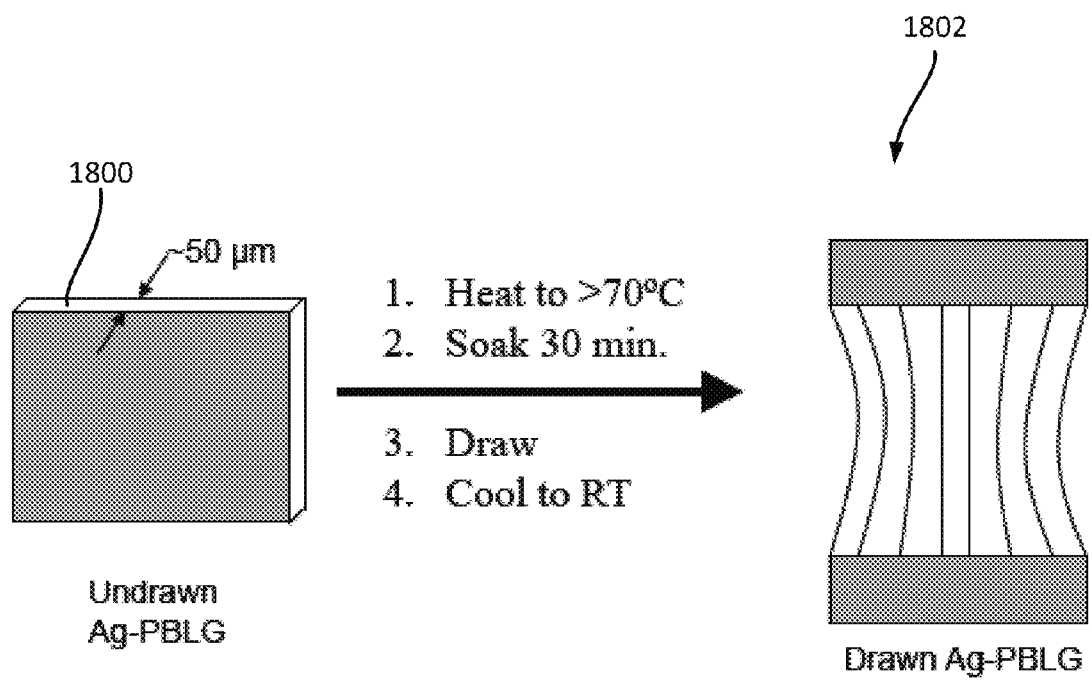

FIG. 18 illustrates a method for providing/manufacturing a composite material that includes drawing the composite material.

Figure 19:
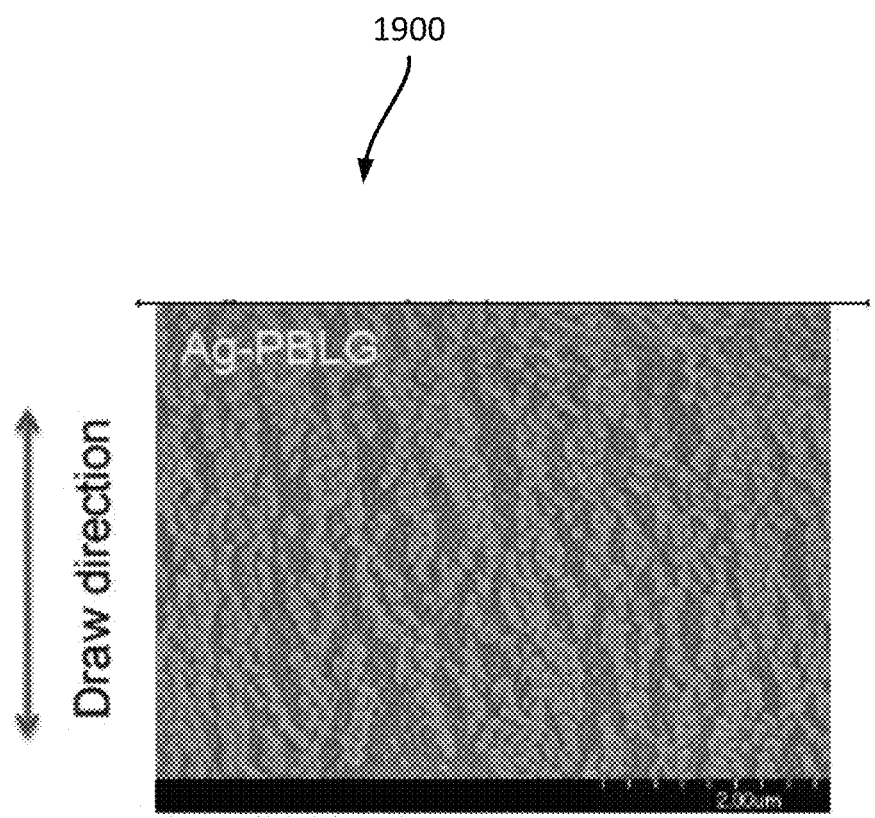

FIG. 19 illustrates a scanning electron micrograph (SEM) of a drawn DCPM (Ag-PBLG).

Figure 20:
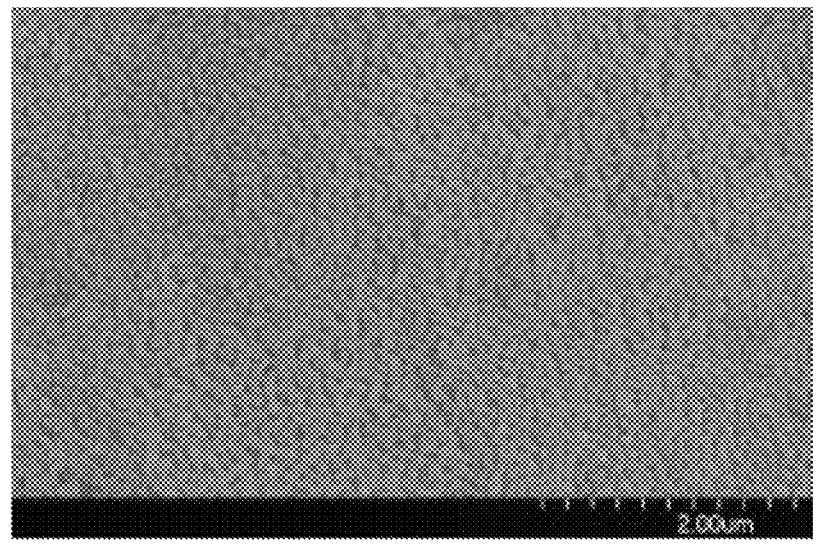

FIG. 20 illustrates a scanning electron micrographs (SEM) of an undrawn DCPM (Ag-PBLG).

Figure 21:
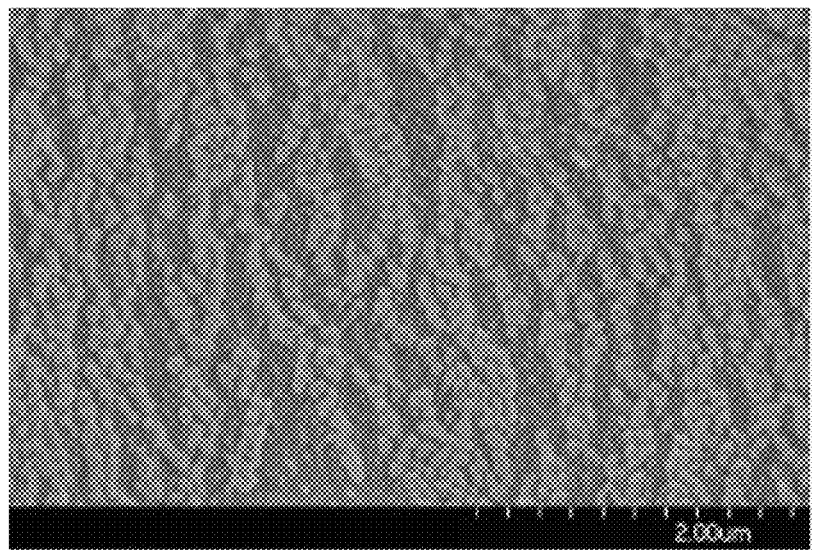

FIG. 21 illustrates a scanning electron micrographs (SEM) of a drawn DCPM (Ag-PBLG).

Figure 22:
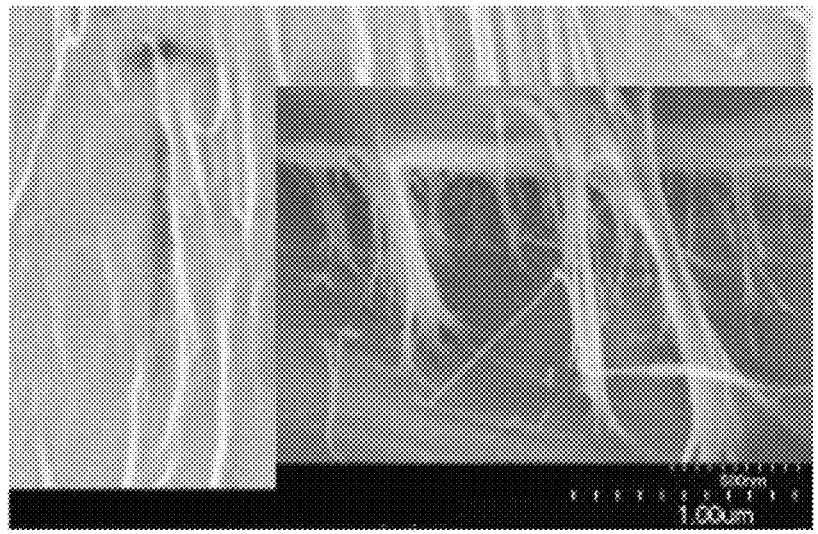

FIG. 22 illustrates a scanning electron micrographs (SEM) of an undrawn and a drawn (inset) DCPM (Ag-PBLG).

Figure 23:
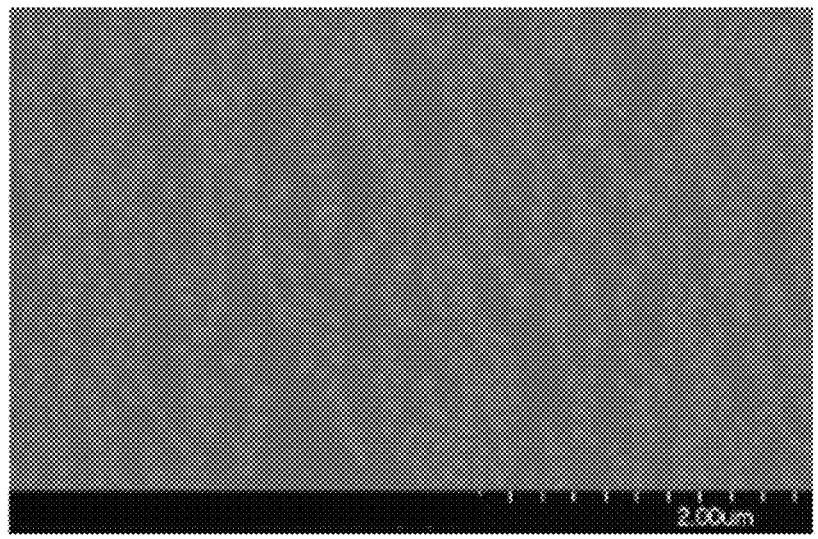

FIG. 23 illustrates a scanning electron micrographs (SEM) of a drawn DCPM (Ag-PBLG).

Figure 24:
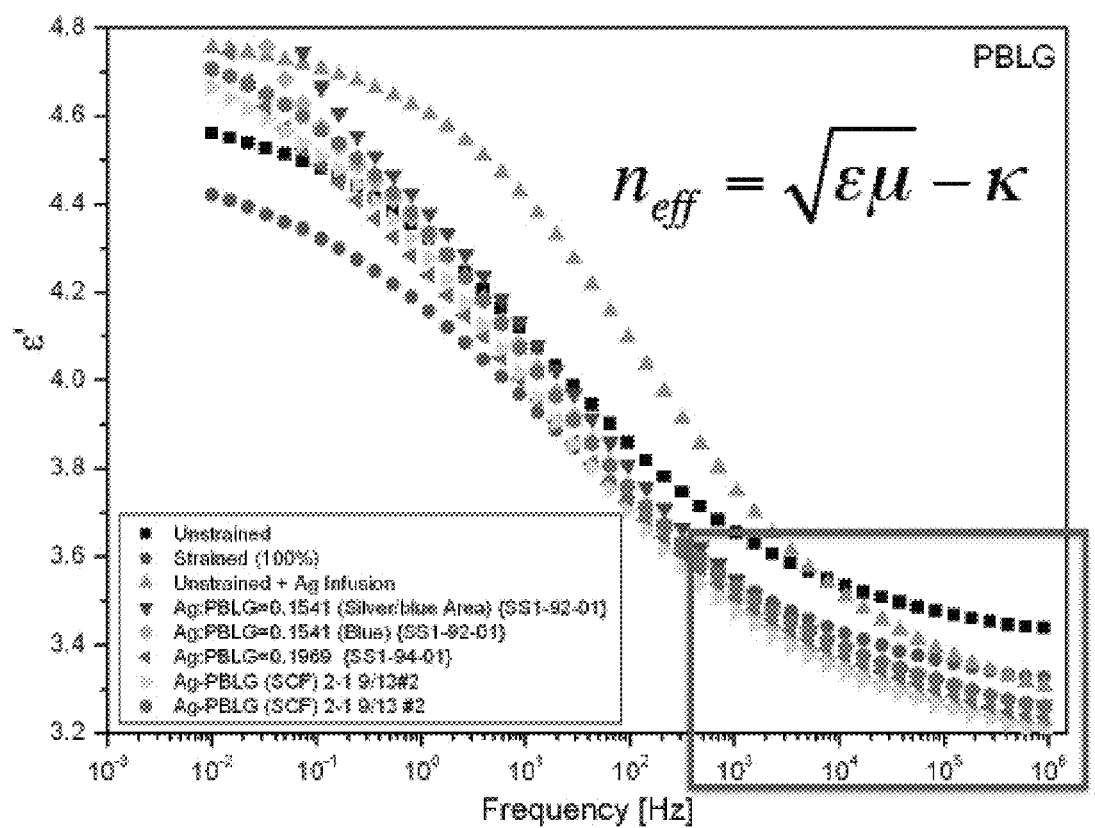

FIG. 24 illustrates the permittivity of various composite materials as a function of frequency.

Figure 25:
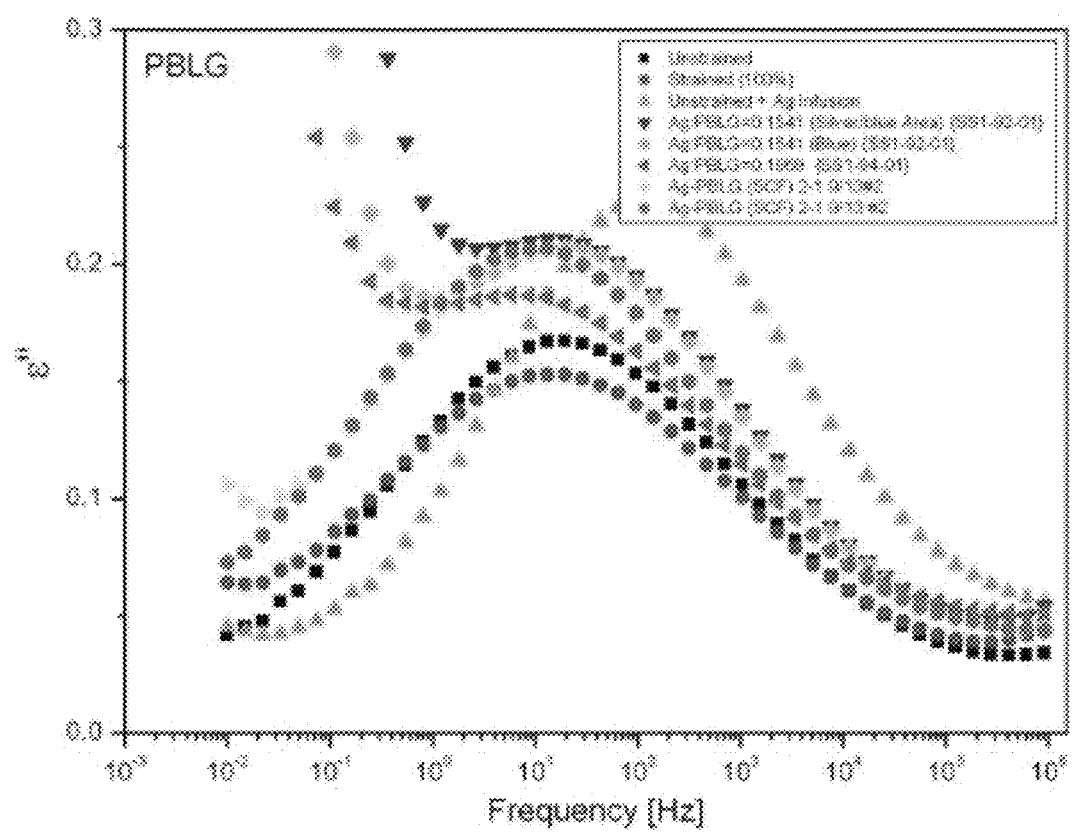

FIG. 25 illustrates the loss permittivity of various composite materials as a function of frequency.

Figure 26:
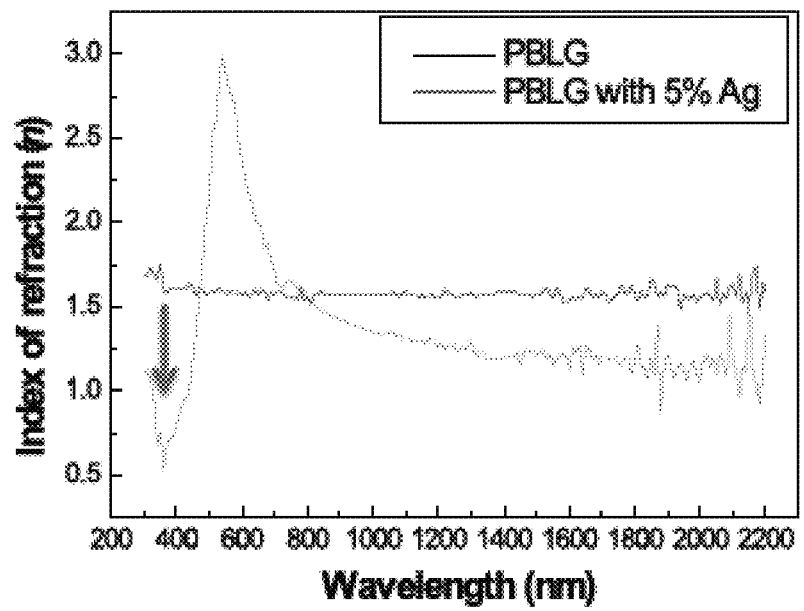

FIG. 26 illustrates the index of refraction of various composite materials along different wavelengths of the electromagnetic spectrum.

Figure 27:
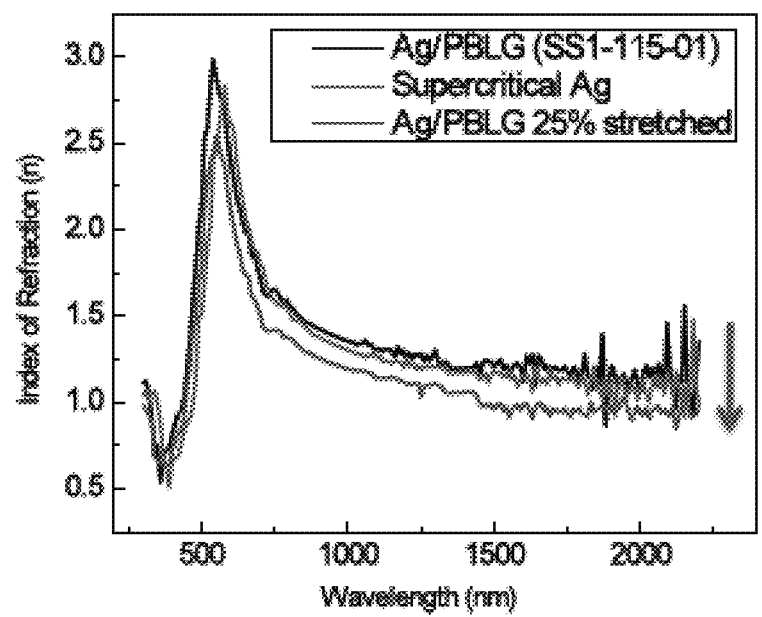

FIG. 27 illustrates the index of refraction of various composite materials along different wavelengths of the electromagnetic spectrum.

SUMMARY

Some implementations provide a composite material that includes a first material and a second material. The first material includes a chiral polymer. The second material is within the chiral polymer. The first material and the second material are configured to provide an effective index of refraction value for the composite material of 1 or less.

According to an aspect, the effective index of refraction value for the composite material is negative.

According to one aspect, the effective index of refraction value for the composite material of 1 or less is at least in a wavelength of one of at least a visible spectrum, an infrared spectrum, a microwave spectrum, and/or an ultraviolet spectrum.

According to an aspect, the composite material has a negative permittivity value. In some implementations, the composite material has zero or greater permittivity value.

According to one aspect, the composite material has a negative permeability value. In some implementations, the composite material has zero or greater permeability value.

According to an aspect, the effective index of refraction value for the composite material is based on at least a chiral parameter of the composite material.

According to one aspect, the first material has a first chiral parameter and the composite material has a second chiral parameter. The second material is configured to cause the second chiral parameter of the composite material to be greater than the first chiral parameter of the first material.

According to an aspect, the chiral polymer includes one of at least a crystalline chiral helical polymer, poly-γ-benzyl-L-glutamate (PBLG), poly-L-lactic acid (PLA), polypeptide, and/or polyacetylene.

According to one aspect, the second material is one of at least a dopant and/or an inclusion.

According to an aspect, the second material is one of at least ionic dopant, phosphoric acid ($H_3PO_4$), sulfuric acid ($H_2SO_4$), triflic acid ($CF_3SO_3H$), imidazole ($C_3H_4N_2$), lithium perchlorate ($LiClO_4$), ammonium perchlorate ($NH_4ClO_4$), and/or lithium iodine (LiI).

According to one aspect, the second material is one of at least nanoparticles, nanotubes, nanoplatelets, and/or nanowires. In some implementations, the nanotube is one of at least a carbon nanotube (CNT), a boron nitride nanotube (BNNT), and/or a boron carbide nitride nanotube (BCNNT).

According to an aspect, the second material is a plasmonic inclusion comprising one of at least silver (Ag) and/or gold (Au).

According to one aspect, the second material is aligned along a particular direction in the first material. In some implementations, the second material being aligned along the particular direction causes the composite material to have a greater chiral parameter.

According to an aspect, the composite material is stretched along a particular direction. In some implementations, the composite material being stretched along the particular direction causes the composite material to have a greater chiral parameter.

According to one aspect, the composite material is configured to be incorporated in one of at least a device configured for beam steering, a miniature solid state filter, an ultra-thin backwards antenna, a super lens, an optical limiter, a supersensitive sensor, and/or a cloaking device.

Some implementations provide a composite material that includes a first material and a second material. The first material includes a chiral polymer. The second material is within the chiral polymer such that the composite material has a first resonant frequency in a visible spectrum and a second resonant frequency in one of at least an infrared spectrum, a microwave spectrum, and/or an ultraviolet spectrum from an electromagnetic spectrum.

According to an aspect, the composite material has an effective index of refraction value of 1 or less.

According to one aspect, the composite material has a negative effective index of refraction value.

According to an aspect, the composite material has a negative permittivity value. In some implementations, the composite material has zero or a positive permittivity value.

According to one aspect, the composite material has a negative permeability value. In some implementations, the composite material has zero or a positive permeability value.

According to an aspect, the first material has a first chiral parameter and the composite material has a second chiral parameter. The second material is configured to cause the second chiral parameter of the composite material to be greater than the first chiral parameter of the first material.

According to one aspect, the chiral polymer includes one of at least a crystalline chiral helical polymer, poly-γ-benzyl-L-glutamate (PBLG), poly-L-lactic acid (PLA), polypeptide, and/or polyacetylene.

According to an aspect, the second material is one of at least a dopant and/or an inclusion.

According to one aspect, the second material is one of at least ionic dopant, phosphoric acid ($H_3PO_4$), sulfuric acid ($H_2SO_4$), triflic acid ($CF_3SO_3H$), imidazole ($C_3H_4N_2$), lithium perchlorate ($LiClO_4$), ammonium perchlorate ($NH_4ClO_4$), and/or lithium iodine (LiI).

According to an aspect, the second material is one of at least nanoparticles, nanotubes, nanoplatelets, and/or nanowires. In some implementations, the nanotube is one of at least a carbon nanotube (CNT), a boron nitride nanotube (BNNT), and/or a boron carbide nitride nanotube (BCNNT).

According to one aspect, the second material is a plasmonic inclusion comprising one of at least silver (Ag) and/or gold (Au).

According to an aspect, the second material is aligned along a particular direction in the first material. The second material being aligned along the particular direction causes the composite material to have a greater chiral parameter.

According to one aspect, the composite material is stretched along a particular direction. The composite material being stretched along the particular direction causes the composite material to have a greater chiral parameter.

According to an aspect, the composite material is configured to be incorporated in one of at least a device configured for beam steering, a miniature solid state filter, an ultra-thin backwards antenna, a super lens, an optical limiter, a super-sensitive sensor, and/or a cloaking device.

Some implementations provide a composite material that includes a first material and a second material. The first material includes a chiral polymer. The second material is within the chiral polymer. The composite material is configurable to have a first index of refraction when the second material is under a first external stimuli and a second index of refraction when the second material is under a second external stimuli.

According to an aspect, the first external stimuli is a zero external field.

According to one aspect, the first and second external stimulus are one of at least an electric field, a magnetic field, and/or a photoelectric effect.

According to an aspect, the first index of refraction is the first index of refraction at a first frequency, and the second index of refraction is the second index of refraction at the first frequency.

DETAILED DESCRIPTION

In the following description, specific details are given to provide a thorough understanding of the various aspects of the disclosure. However, it will be understood by one of ordinary skill in the art that the aspects may be practiced without these specific details.

Overview

Some implementations provide a composite material that includes a first material and a second material. In some implementations, the composite material is a metamaterial. The first material includes a chiral polymer (e.g., crystalline chiral helical polymer, poly-γ-benzyl-L-glutamate (PBLG), poly-L-lactic acid (PLA), polypeptide, and/or polyacetylene). The second material is within the chiral polymer. The first material and the second material are configured to provide an effective index of refraction value for the composite material of 1 or less. In some implementations, the effective index of refraction value for the composite material is negative. In some implementations, the effective index of refraction value for the composite material of 1 or less is at least in a wavelength of one of at least a visible spectrum, an infrared spectrum, a microwave spectrum, and/or an ultraviolet spectrum.

In some implementations, the composite material has a positive (e.g., zero or greater) or negative permittivity value. In some implementations, the composite material has a positive (e.g., zero or greater) or negative permeability value. In some implementations, the effective index of refraction value for the composite material is based on at least a chiral parameter of the composite material. In some implementations, the effective index of refraction value for the composite material is based on a first index of refraction value for the first material and a change in an index of refraction value for the second material.

In some implementations, the first material has a first chiral parameter and the composite material has a second chiral parameter. The second material (e.g., inclusion) is configured to cause the second chiral parameter of the composite material to be greater than the first chiral parameter of the first material. In some implementations, the second material (e.g., inclusion) is aligned along a particular direction in the first material, where the second material being aligned along the particular direction causes the composite material to have a greater chiral parameter. In some implementations, the composite material is stretched along a particular direction, where the composite material being stretched along the particular direction causes the composite material to have a greater chiral parameter.

In some implementations, the second material is one of at least a dopant and/or an inclusion. In some implementations, the second material is one of at least ionic dopant, phosphoric acid ($H_3PO_4$), sulfuric acid ($H_2SO_4$), triflic acid ($CF_3SO_3H$), imidazole ($C_3H_4N_2$), lithium perchlorate (Li$ClO_4$), ammonium perchlorate ($NH_4ClO_4$), and/or lithium iodine (LiI). In some implementations, the second material is one of at least plasmonic inclusions, nanoparticles, nanotubes, nanoplatelets and/or nanowires. In some implementations, the plasmonic inclusion is one of at least silver (Ag) and/or gold (Au). In some implementations, the nanotube is one of at least a carbon nanotube (CNT), a boron nitride nanotube (BNNT), and/or a boron carbide nitride nanotube (BCNNT).

Some implementations also provide a composite material that includes a first material and a second material. In some implementations, the composite material is a metamaterial. The first material is a chiral polymer (e.g., a crystalline chiral helical polymer, poly-γ-benzyl-L-glutamate (PBLG), poly-L-lactic acid (PLA), polypeptide, and/or polyacetylene). The second material is within the chiral polymer such that the composite material has a first resonant frequency in a visible spectrum and a second resonant frequency in one of at least an infrared spectrum, a microwave spectrum, and/or an ultraviolet spectrum from an electromagnetic spectrum. In some implementations, the chiral polymer is configured to provide the composite material with the first resonant frequency in the visible spectrum. In some implementations, the first resonant frequency is in the ultraviolet/visible spectrum. In some implementations, the second material (e.g., dopant, inclusion) is configured to provide the composite material with the second resonant frequency in one of at least the infrared spectrum, the microwave spectrum, and/or the ultraviolet spectrum from the electromagnetic spectrum.

Exemplary Composite Material Comprising Chiral Material

Figure 1:
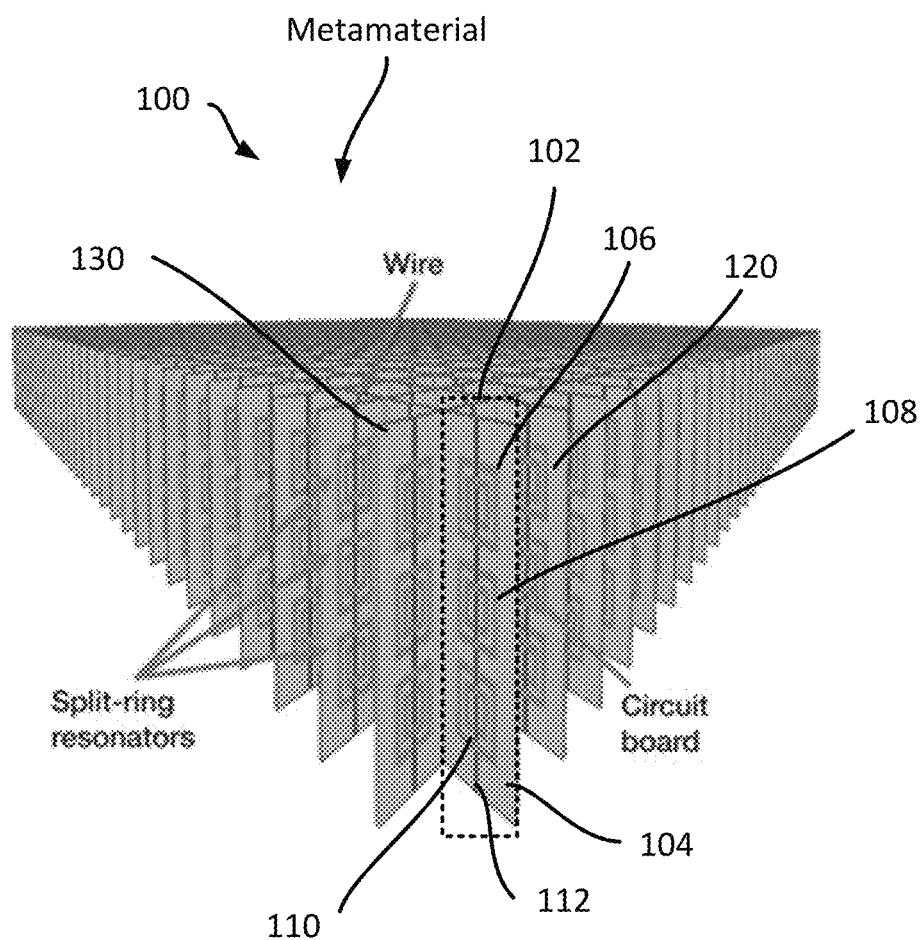
FIG. 1 illustrates an example of a current metametarial.
Figure 2:
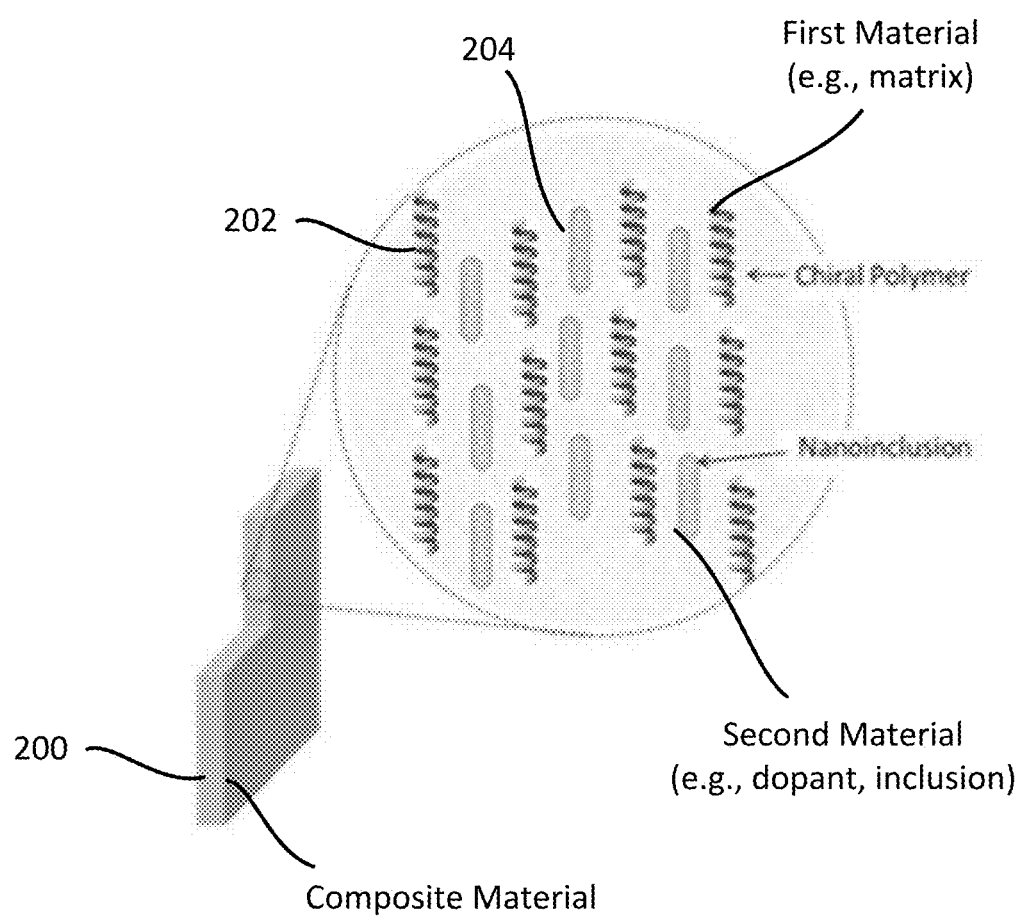
FIG. 2 illustrates a conceptual example of a composite material that includes a chiral polymer and a nanoinclusion.

FIG. 2 illustrates a conceptual example of a composite material comprising a chiral component. Specifically, FIG. 2 illustrates an aligned composite material 200 that includes a chiral component, a dopant or an inclusion. In some implementations, the composite material is a metamaterial. In some implementations, the chiral component (e.g., first material, base material, host material) is a component that is non-superposable on its mirror image through translation and/or rotation. As such, an object, medium and/or material (e.g., chiral component) is chiral when the object, medium and/or the material is non-superposable on its mirror image through translation and/or rotation. In some implementations, the chiral component is a chiral polymer 202. In some implementations, the inclusion (e.g., second material) is a nano-inclusion 204, (plasmonic nano-inclusions). Different implementations may use different materials for the chiral component, the dopant (e.g., second material) and/or the inclusion (e.g., second material).

In some implementations, the chiral polymer (e.g., first material of the composite material) includes one of at least a crystalline chiral helical polymer, poly-γ-benzyl-L-glutamate (PBLG), poly-L-lactic acid (PLA), polypeptide, and/or polyacetylene. However, different implementations may user different materials and/or polymers.

In some implementations, the second material is one of at least phosphoric acid ($H_3PO_4$), sulfuric acid ($H_2SO_4$), triflic acid ($CF_3SO_3H$), imidazole ($C_3H_4N_2$), lithium perchlorate (LiClO$_4$), ammonium perchlorate ($NH_4ClO_4$), and/or lithium iodine (LiI). In some implementations, the second material is one of at least plasmonic inclusions, nanotubes and/or nanowires. In some implementations, the plasmonic inclusions is one of at least silver (Ag) and/or gold (Au). In some implementations, the nanotube is one of at least a carbon nanotube (CNT), a boron nitride nanotube (BNNT), and/or a boron carbide nitride nanotube (BCNNT).

The term "composite material" as used herein is defined to include a material that has two or more different materials (e.g., first material, second material, third material, etc. . . . ). In some implementations, the materials in the composite material may have the same state or have different states. In some implementations, a composite material may be a metamaterial. In some implementations, a composite material may include two or more materials that is homogenous in the composite material. That is, in some implementations, a composite material may include a homogenous material that has relatively the same property across the entire material (e.g., behaves the same across the entire material, has the same electromagnetic property across the entire material). In some implementations, a composite material may include two or more materials that remain separate and distinct in the composite material. A composite material may be provided, manufactured, created by using mixing and/or a chemical process.

FIGS. 3-9 illustrate various examples of a composite material that includes a chiral component. Specifically, FIGS. 3-8 illustrate scanning electron micrographs (SEM) illustrations of various composite materials that include a chiral component (e.g., chiral polymer).

Figure 3:
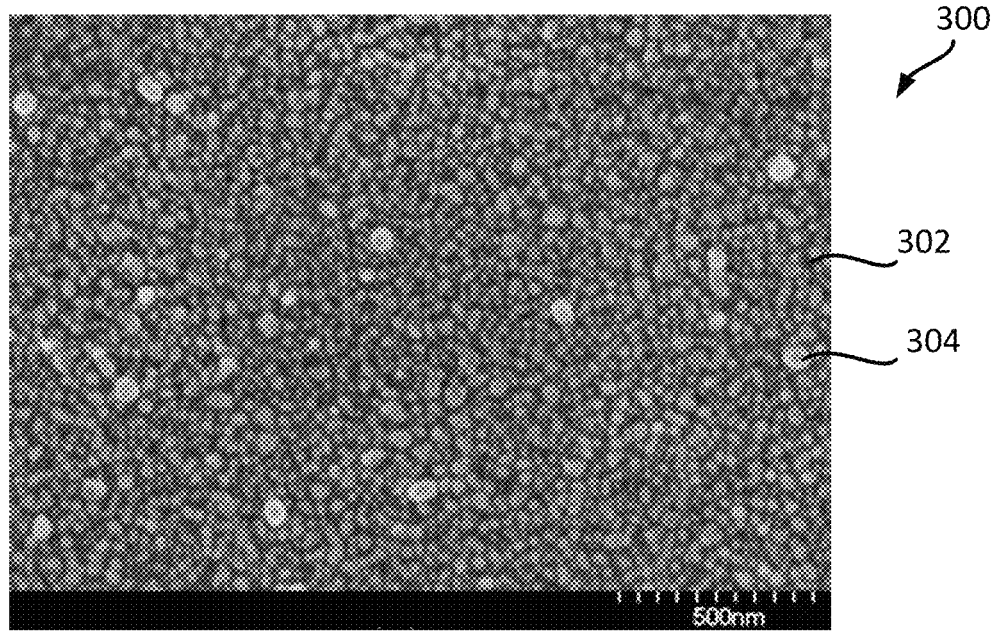
FIG. 3 illustrates an example of a composite material that includes a chiral polymer and plasmonic nanoinclusions processed by direct mixing with a metal precursor and a chiral polymer.

FIG. 3 illustrates a composite material 300 that includes a first material 302 and a second material 304. In some implementations, the composite material 300 is a metamaterial. The first material 302 (darker shade material) is a chiral polymer that includes poly-γ-benzyl-L-glutamate (PBLG), in some implementations. The second material 304 (lighter shade material) is an inclusion that includes silver (Ag). In some implementations, the second material 304 is a plasmonic nano-inclusion. In some implementations, the composite material 300 is manufactured using direct mixing. The use of direct mixing to manufacture a composite material (e.g., composite material 300) will be further described below.

Figure 4:
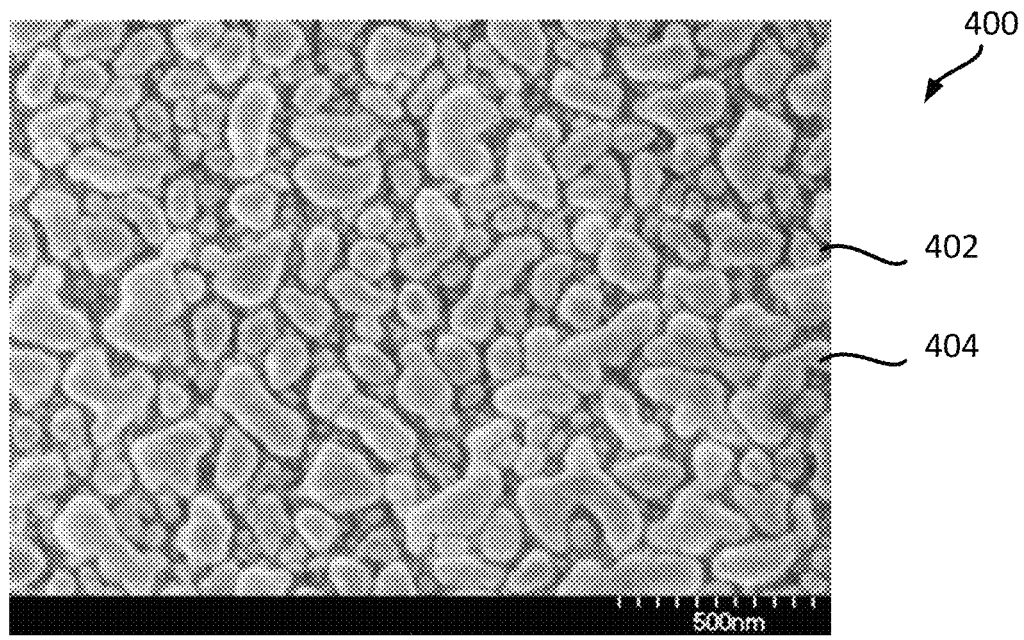
FIG. 4 illustrates an example of a composite material that includes a chiral polymer and plasmonic nanoinclusions processed by supercritical fluid infusion.

FIG. 4 illustrates a composite material 400 that includes a first material 402 and a second material 404. In some implementations, the composite material 400 is a metamaterial. The first material 402 (darker shade material) is a chiral polymer that includes poly-γ-benzyl-L-glutamate (PBLG), in some implementations. The second material 404 (lighter shade material) is an inclusion that includes silver (Ag). In some implementations, the second material 304 is a plasmonic nano-inclusion. In some implementations, the composite material 400 is manufactured using super critical fluid (SCF) infusion. The use of super critical fluid (SCF) infusion to manufacture a composite material (e.g., composite material 400) will be further described below.

Figure 5:
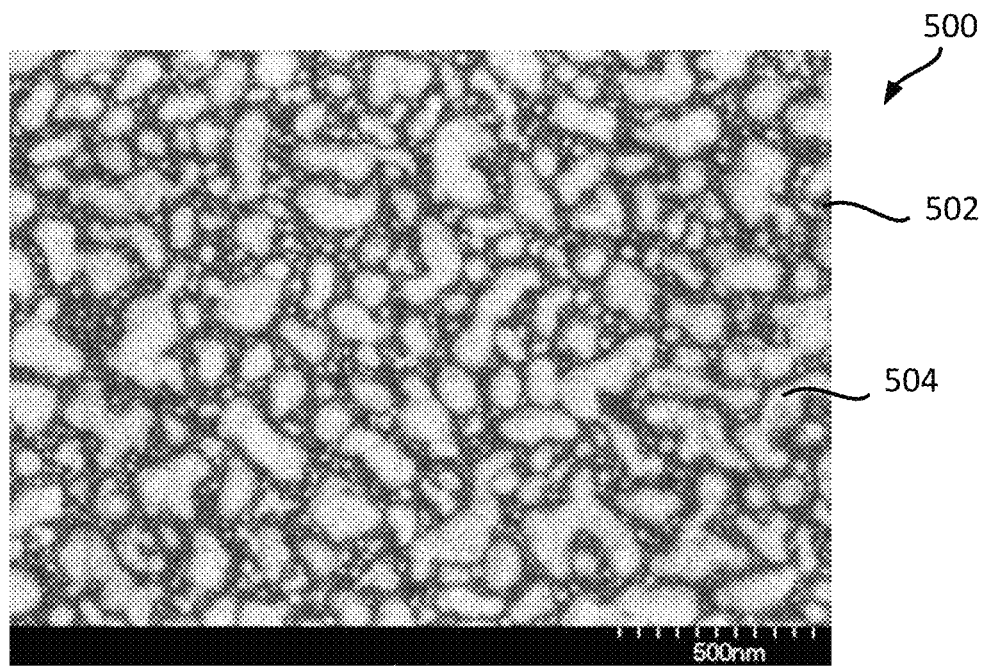
FIG. 5 illustrates an example of a composite material that includes a chiral polymer and plasmonic nanoinclusions processed by supercritical fluid infusion.

FIG. 5 illustrates a composite material 500 that includes a first material 502 and a second material 504. In some implementations, the composite material 500 is a metamaterial. The first material 502 (darker shade material) is a chiral polymer that includes poly-γ-benzyl-L-glutamate (PBLG), in some implementations. The second material 504 (lighter shade material) is an inclusion that includes silver (Ag). In some implementations, the second material 504 is a plasmonic nano-inclusion. In some implementations, the composite material 500 is manufactured using super critical fluid (SCF) infusion.

Figure 6:
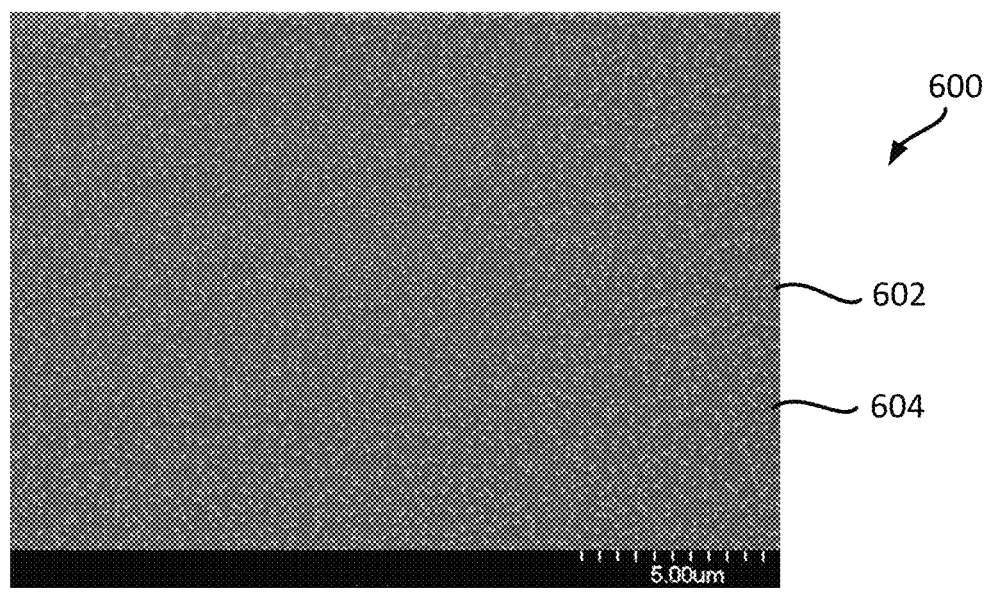
FIG. 6 illustrates an example of a composite material that includes a chiral polymer and plasmonic nanoinclusions processed by supercritical fluid infusion.

FIG. 6 illustrates a composite material 600 that includes a first material 602 and a second material 604. In some implementations, the composite material 600 is a metamaterial. The first material 602 (darker shade material) is a chiral polymer that includes poly-γ-benzyl-L-glutamate (PBLG), in some implementations. The second material 604 (lighter shade material) is an inclusion that includes silver (Ag). In some implementations, the composite material 600 is manufactured using super critical fluid (SCF) infusion.

Figure 7:
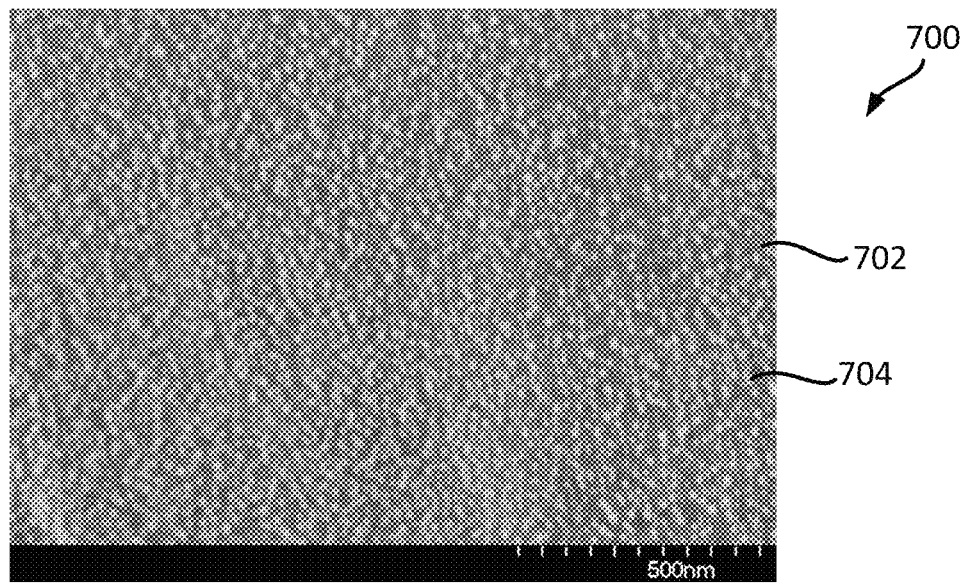
FIG. 7 illustrates an example of a composite material that includes a chiral polymer and plasmonic nanoinclusions.

FIG. 7 illustrates a composite material 700 that includes a first material 702 and a second material 704. In some implementations, the composite material 700 is a metamaterial. The first material 702 (lighter shade material) is chiral polymer that includes poly-γ-benzyl-L-glutamate (PBLG), in some implementations. The second material 704 (lighter shade material) is an inclusion that includes silver (Ag). In some implementations, the second material 704 is a plasmonic nano-inclusion. In some implementations, the composite material 700 is manufactured using super critical fluid (SCF) infusion.

Figure 8:
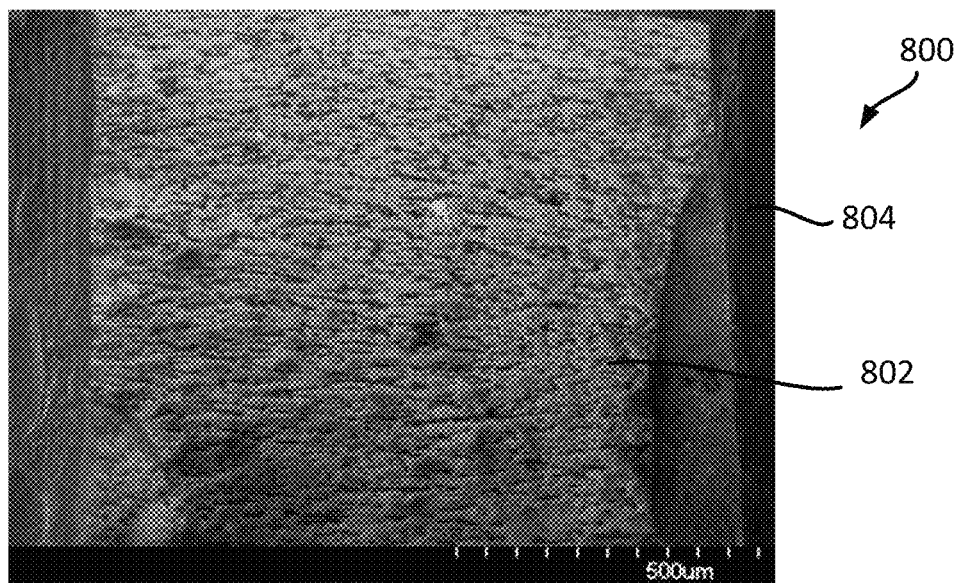
FIG. 8 illustrates a conceptual example of a composite material that includes a polymer and aligned single wall carbon nanotubes.

FIG. 8 illustrates a composite material 800 that includes a first material 802 and a second material 804. The first material 802 is a polymer that includes poly-γ-benzyl-L-glutamate (PBLG), in some implementations. The second material 804 is an inclusion that includes single wall carbon nanotubes (SWCNT). In some implementations, the composite material 800 is a metamaterial. In some implementations, the SWCNT are aligned in the composite material 800. The alignment of the SWCNT in the composite material 800 may be performed by applying an electric field on the SWCNT in some implementations during the manufacturing of the composite material.

Figure 9:
FIG. 9 illustrates an example of a plasmonic nanometal doped chiral polymer metamaterial (Ag doped PBLG).

FIG. 9 illustrates a composite material 900 that includes a first material and a second material. The composite material 900 is a film composite material. In some implementations, the composite material 900 is a metamaterial. Specifically, the composite material 900 is a silver (Ag)/poly-γ-benzyl-L-glutamate (PBLG) composite material, in some implementations. The first material is a chiral polymer that includes poly-γ-benzyl-L-glutamate (PBLG), in some implementations. The second material is an inclusion that includes silver (Ag). In some implementations, the second material 704 is a plasmonic nano-inclusion. In some implementations, the composite material 900 is manufactured direct mixing or using super critical fluid (SCF) infusion.

It should be noted that FIGS. 3-9 are merely examples of a composite materials that includes a chiral component (e.g., chiral polymer). In some implementations, the composite material may include other materials for the first and/or second materials.

Having described examples of various composite materials, several properties of these composite materials will now be described.

Exemplary Properties of Composite Material Comprising Chiral Material

In some implementations, the composite material (e.g., composite material 200) in the present disclosure is an electromagnetic material with unique and/or exotic electromagnetic properties. Exemplary material properties of interest for a composite material include chiral parameter (κ), permittivity (∈), permeability (μ), index of refraction (n), and resonant frequency. These exemplary material properties will be described with respect to the composite material 200. However, these exemplary material properties are applicable to any of the composite materials in the present disclosure. In addition, the individual components/materials (e.g., first material, second material, chiral polymer, inclusion) that are within the composite material may also have its own respective properties (e.g., electromagnetic properties). In some implementations, the properties of these materials may affect the overall (e.g., effective) properties of the composite materials.

(a) Chiral Parameter

In some implementations, the chiral parameter (κ) of a material defines and/or quantifies the degree of chirality of the material. In some implementations, the chirality of a material defines the handedness of the material. In some implementations, the handedness of a material may be represented as right-handed or left-handed. The chiral parameter (κ) is between zero (0) and unity (1), in some implementations. In some implementations, the chiral parameter (κ) of a material quantifies how right-handed or left-handed the material is.

In some implementations, the composite material may have a chiral parameter. In addition, material that are in the composite material may have their its own respective chiral parameters. For example, a first material (e.g., chiral polymer) may have a first chiral parameter, and a second material (e.g., inclusion) may have a second chiral parameter. One or more of these chiral parameters may affect other properties of the composite materials. For example, one or more of these chiral parameters may affect the index of refraction of a composite material.

(b) Permittivity

In some implementations, the permittivity ($\in$) of a material defines the resistance that is encountered when forming an electric field in the material. In some implementations, permittivity ($\in$) is a measure of how an electric field affects, and is affected by, a dielectric medium. The permittivity of a material (e.g., composite material) may be positive, zero, or negative in some implementations.

(c) Permeability

In some implementations, the permeability (μ) of a material defines the degree of magnetization of the material in response to a magnetic field. In some implementations, the permeability (μ) of the material is the measure of the ability of the material to support the formation of a magnetic field within itself. The permeability of a material (e.g., composite material) may be positive, zero, or negative in some implementations.

(d) Index of Refraction

In some implementations, the index of refraction (n) of a material is a dimensionless number that describes how light, or any other radiation (e.g., electromagnetic spectrum), propagates through that material (e.g., medium). In some implementations, the index of refraction is defined as follows:

$$n = \frac{c}{v},$$

where c is the speed of light in vacuum and v is the speed of light in the material. In some implementations, the index of refraction of a material varies with the wavelength. That is a material may have different index of refraction for different wavelength. This concept is known as dispersion. All light in vacuum (e.g., empty space) will have an index of refraction of 1. Naturally occurring materials have an index of refraction greater than 1.

In some implementations, the index of refraction of a composite material that includes the chiral component may have an index of refraction that is 1 or less. In some implementations, the composite material that includes the chiral index will have several different indices of refractions that are 1 or less. For example, the composite material (e.g., composite material 200) may have a first index of refraction that is 1 or less for a first wavelength, and a second index of refraction that is 1 or less for a second wavelength.

In some implementations, the index of refraction of a composite material that includes the chiral component may have an index of refraction that is negative. In some implementations, the composite material that includes the chiral index will have several different indices of refractions that are negative. For example, the composite material (e.g., composite material 200) may have a first index of refraction that is negative for a first wavelength, and a second index of refraction that is negative for a second wavelength.

In some implementations, the composite material (e.g., composite material 200) is configured in such a way as to have an effective index of refraction of less than 1 and/or an effective index of refraction that is negative (e.g., first index of refraction that is one or less, second index of refraction that is negative). In some implementations, the composite material (e.g., composite material 200) is configured in such a way as to have an effective index of refraction of 1 or less and/or an effective index of refraction that is negative, for one or more wavelengths in the electromagnetic spectrum (e.g., visible, ultraviolet, microwave, infrared).

In some implementations, the effective index of refraction of a composite material takes into account (e.g., is based on) the chiral parameter of the host material (e.g., first material, chiral component) and/or the chiral parameter of the composite material. In some implementations, the effective index of refraction ($n_{eff}$) is defined as follows:

$$n_{eff} = \sqrt{\in \mu} - \kappa$$

where $\in$ is the effective permittivity of the composite material, μ is the effective permeability of the composite material, and κ is the chiral parameter of the chiral component.

In some implementations, the effective index of refraction ($n_{eff}$) can also be defined as follows:

$$n_{eff} = n_{composite} - \kappa_{composite}$$

where $n_{composite}$ is the index of refraction of the composite material and $\kappa_{composite}$ is the chiral parameter of the composite material.

In some implementations, the index of refraction of the composite material ($n_{composite}$) may be defined as follows:

$$n_{composite} = n_{host} - \Delta n_{plasmonic}$$

where $n_{host}$ is the index of refraction of the host material (e.g., first material, chiral component) and $\Delta n_{plasmonic}$ is the change in the index of refraction of the dopant and/or inclusion (e.g., nanotube, nanowire).

(e) Resonant Frequency

In some implementations, a resonant frequency of a material (e.g., composite material 200) is the frequency at which the response of the material to an oscillatory stimulus is greater than at other frequencies.

In some implementations, the composite material 200 is configured in such a way as to have a resonant frequency in one or more different frequency spectrums. In some implementations, the composite material 200 is configured to have resonant frequencies over a broader spectrum of the wavelengths (e.g., electromagnetic spectrum) than current natural materials and/or engineered materials.

The electromagnetic spectrum includes the radio spectrum, the microwave spectrum, the infrared spectrum, the visible spectrum, the ultraviolet spectrum, the x-ray spectrum, and the gamma ray spectrum. In some implementations, the radio spectrum includes frequencies of about 300 GHz-3 Hz. In some implementations, the microwave spectrum includes frequencies of 300 GHz-300 MHz. In some implementations, the infrared spectrum includes frequencies of 430 THz-300 GHz. In some implementations, the visible spectrum includes frequencies of 790 THz-430 THz. In some implementations, the ultraviolet spectrum includes frequencies of 30 PHz-790 THz. In some implementations, the x-ray spectrum includes frequencies of 30 EHz-30 PHz. In some implementations, the gamma ray spectrum includes frequencies of more than 10 EHz. It should be noted that the range of frequencies of each region of the electromagnetic spectrum is merely exemplary. In addition, each of these spectrums (e.g., visible, ultraviolet, microwave, infrared) has corresponding wavelength ranges, which is known in the art.

In some implementations, the composite material 200 is configured to have one or more resonant frequencies in the visible spectrum. In some implementations, the composite material 200 is configured to have one or more resonant frequencies in the infrared spectrum, the visible spectrum, and/or the ultraviolet spectrum. In some implementations, the composite material 200 is configured to have one or more resonant frequencies in the microwave spectrum. In some implementations, the composite material 200 has a first resonant frequency in a visible spectrum and a second resonant frequency in one of at least an infrared spectrum, a microwave spectrum, and/or an ultraviolet spectrum from an electromagnetic spectrum.

In some implementations, the spectrum in which the composite material 200 will have one or more resonant frequencies may be specified by providing different combinations and/or configurations of the chiral component (e.g., chiral polymer), the dopant and/or the inclusion. Examples of combinations and/or configurations of the composite material 200 include (i) different materials for the chiral component, the dopant and/or the inclusion, (ii) different composition of chiral component, the dopant and/or the inclusion, (iii) different orientation of the dopant and/or inclusion, (iv) different size of the chiral component, the dopant and/or the inclusion, (vi) different aspect ratios of the chiral component, the dopant and/or the inclusion, (vii) different alignment of the chiral component, the dopant and/or the inclusion, (viii) different spacing between the chiral component, the dopant and/or the inclusion, and (ix) different types and intensity of external fields (e.g., electric, magnetic, photoelectric, mechanical) when manufacturing the composite material. Examples of such combinations and/or configurations of the chiral component, the dopant and/or the inclusion for the composite material 200 will be further described below.

Exemplary Effect of Properties in Composite Material

Different implementations may have different combinations of the above properties (e.g., electromagnetic properties). For example, different implementations may have different combinations of permittivity, permeability, chiral parameter, index of refraction and/or resonant frequencies.

For example, in some implementations, the composite material 200 may be configured to have a positive permittivity ($\in$) value (e.g., value zero or greater) and a positive permeability value ($\mu$) (e.g., value that is less than zero). In some implementations, the composite material may be configured to have a positive permittivity ($\in$) value (e.g., value zero or greater) and a negative permeability value ($\mu$) (e.g., value that is less than zero).

In both exemplary instances, the composite material 200 may have an index of refraction that is 1 or less and/or negative in some implementations. When the composite material 200 has a negative index of refraction, the composite material 200 is a negative index of refraction material (NIM). In some implementations, a NIM is a material that has optical properties that is opposite to glass, air, and other transparent media. In some implementations, a NIM is opaque to electromagnetic radiation.

In some implementations, the addition of the second material (e.g., inclusion) lowers the effective permittivity of the composite material. Moreover, in some implementations, performing certain operations/processes (e.g., drawing, aligning) on the composite materials, the first material, and/or the second material may lower the effective permittivity of the composite material. These operations/processes will be further described below.

In some implementations, the addition of the second material (e.g., inclusion) increases the effective chiral parameter of the composite material. Moreover, in some implementations, performing certain operations/processes (e.g., drawing, aligning) on the composite materials, the first material, and/or the second material may increase the effective chiral parameter of the composite material. These operations/processes will be further described below.

In some implementations, the result of higher chiral parameter for the material (e.g., composite material, first material, second material) and/or a lower permittivity for the material (e.g., composite material, first material, second material) is an effective index of refraction value for the composite material that 1 or less and/or negative in some implementations. In some implementations, the permeability of the composite material may be positive (e.g., zero or greater) or negative.

Moreover, in some implementations, the composite material is configurable tunable. That is, in some implementations, the composite material may have an index of refraction value that is configurable and/or one or more resonant frequencies that is configurable. In some implementations, the composite material may be configured by applying an electric field on the composite material, which may temporarily align the second material in the composite along a particular direction. In some implementations, the strength of the electric field will determine the angle (e.g., how much angle) at which the second material are aligned in the composite material. The configuration and/or tuning of a composite material will be further described below.

In addition to the above advantages, the composite material 200 also provides a flexible and lightweight material, relative to current metamaterials. The composite material 200 is flexible and lightweight because the composite material avoids the complex geometric structure that is typical in metamaterials. Moreover, the simpler geometric design of the composite material is more cost effective and easier to manufacture than current metamaterials.

Exemplary Materials for Composite Material

As described above, the composite material 200 may includes different materials for the chiral component, the dopant and/or the inclusion. In some implementations, the materials provided for the chiral component, the dopant and/or the inclusion provide a composite material that has a negative permittivity (e.g., effective negative permittivity value), a positive permeability (e.g., effective positive permeability value), and an index of refraction (e.g., effective negative index of refraction value) of 1 or less and/or negative. In some implementations, the chiral component is dielectric that has low permittivity (e.g., a low permittivity value). In some implementations, the chiral component is dielectric component that has a permittivity value of about 1 (e.g., $\in \approx 1$).

In some implementations, the chiral component includes several chiral polymer chains. In some implementations, one or more of these chiral polymer chains has a length that is in the same order as the wavelength of visible spectrum of the electromagnetic spectrum. In some implementations the wavelength of the visible spectrum is in the 390 nanometers (nm)-700 nanometers (nm) range. In some implementations, the chiral polymer chain has a length in the 390 nanometers (nm)-700 nanometers (nm) range. In some implementations, the chiral polymer chain having a length that is in the visible spectrum is what allows the composite device to have a resonant frequency in the visible spectrum.

In some implementations, the chiral component includes one of at least a crystalline chiral helical polymer, poly-γ-benzyl-L-glutamate (PBLG), poly-L-lactic acid (PLA), polypeptide, and/or polyacetylene. In some implementations, the crystalline chiral helical polymer is an aligned liquid crystalline chiral helical polymer. As described above, in some implementations, the chiral component includes self-assembled helical structures of chiral molecules. However, different implementations may use different materials for the chiral component.

In some implementations, the dopant includes one of at least ionic dopant, phosphoric acid ($H_3PO_4$), sulfuric acid ($H_2SO_4$), triflic acid ($CF_3SO_3H$), imidazole ($C_3H_4N_2$), lithium perchlorate ($LiClO_4$), ammonium perchlorate ($NH_4ClO_4$), and/or lithium iodine (LiI). In some implementations, the inclusion includes one of at least plasmonic inclusions, nanoparticles, nanotubes, nanoplatelets, and/or nanowires. In some implementations, the plasmonic inclusion is one of at least silver (Ag) and/or gold (Au). Examples of nanotubes include carbon nanotubes (CNT), boron nitride nanotubes (BNNT), and/or boron carbide nitride nanotubes (BCNNT). However, different implementations may use different materials for the dopant and/or inclusion. In some implementations, the nanotubes and/or nanowires are aligned low permittivity materials In addition to using different materials, some implementations may provide different concentrations of the dopant and/or inclusion in the chiral components. In some implementations, different concentrations of the dopant and/or inclusion may produce different resonant frequencies for the composite material (e.g., composite material 200).

In addition, in some implementations, the size of the dopant and/or the inclusion will also affect the resulting resonant frequencies for the composite materials. Moreover, in some implementations, the spacing and/or aspect ratio between the chiral component and the dopant and/or the inclusion will also affect the resulting resonant frequencies for the composite materials. Additionally, in some implementations, the alignment of the dopant and/or the inclusion will also affect the resulting resonant frequencies for the composite materials. In some implementations, the second material (e.g., dopant, inclusion) is configured to provide the composite material with the second resonant frequency in one of at least the infrared spectrum, the microwave spectrum, and/or the ultraviolet spectrum from the electromagnetic spectrum.

In some implementations, the spacing, aspect ratio and/or alignment may be specified by applying an external force/field on the composite material (e.g., chiral component, dopant, and/or inclusion). Examples of external forces/fields include an electric field, a magnetic field, a photoelectric field, and/or a mechanical force. The use and application of an external force and/or external field will be further described below.

In some implementations, the composite material that includes a chiral component (e.g., chiral polymer component) may be drawn out to further enhance, decrease and/or increase certain properties of the composite material. In some implementations, drawing the composite material may include aligning the chiral component along a certain direction. For example, drawing the composite material may include stretching the composite material, which in some implementations also stretches the chiral component. The process of drawing the composite material will be further described below.

Exemplary Method for Providing/Manufacturing a Composite Material

Different implementations may provide/manufacture the composite material (e.g., composite material 200) differently. An example of a method that may be use to manufacture the composite material (e.g., composite material 200) of the present disclosure is described in U.S. Patent Application Publication 2011/0068291, titled "METALLIZED NANOTUBES POLYMER COMPOSITE (MNPC) AND METHODS FOR MAKING SAME", filed Nov. 26, 2008. U.S. Patent Application Publication 2011/0068291 claims priority to U.S. Provisional Application 61/004,520, filed Nov. 28, 2007. Both applications are herein incorporated by reference. In some implementations, both applications describe a method/process of using super critical fluid (SCF) infusion.

Figure 10:
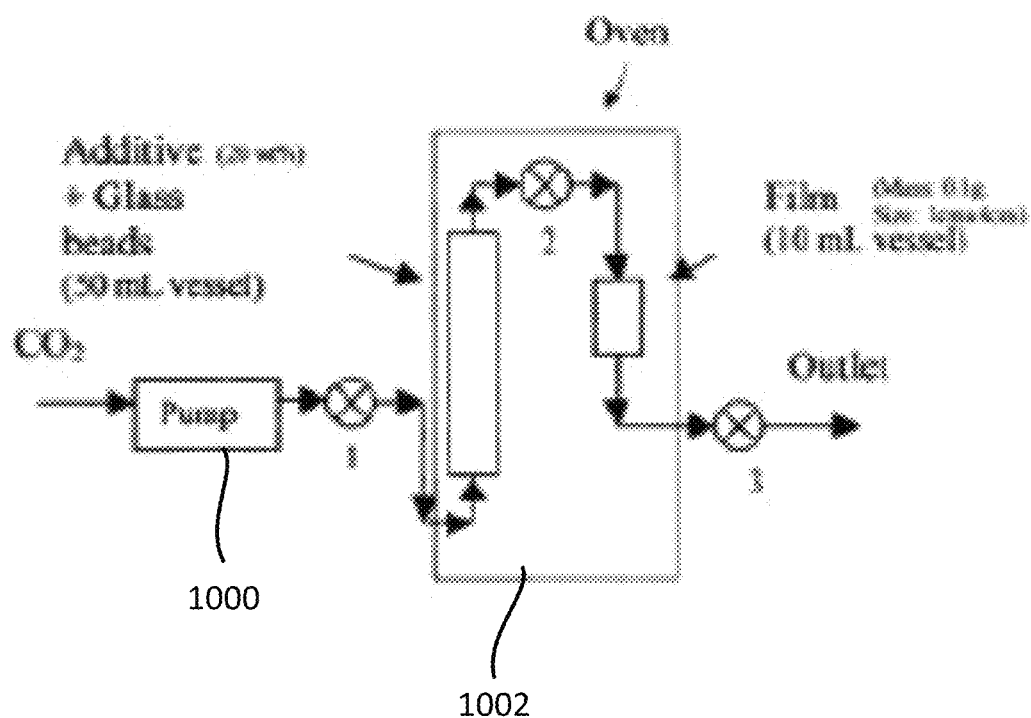
FIG. 10 illustrates a conceptual schematic representation of a method/process of using super critical fluid (SCF) infusion to manufacture a doped chiral polymer metamaterial.

FIG. 10 illustrates a conceptual schematic representation of a method/process of using super critical fluid (SCF) infusion to manufacture a composite material that includes a chiral component. As shown in FIG. 10 a pump 1000 is used to infuse a host material (e.g., polymer, chiral component, poly-γ-benzyl-L-glutamate (PBLG)) with a super critical fluid (SCF). In some implementations, the host material is a chiral polymer component film. In some implementations, the SCF is carbon dioxide ($CO_2$). The combination of the host material and the SCF are provided in an oven 1002. In some implementations, the host material and the SCF are subject to various pressures and temperature for a particular amount of time. In some implementations, the host material (e.g., chiral polymer film) and SCF are subject to a pressure greater than 345.2 atmosphere, a temperature greater than 70 degree Celsius, for a period of time between 1 to 5 hours (e.g., super critical condition). In some implementations, the host material and the SCF are subject to reduction conditions. In some implementations, reduction condition subjected the host material and the SCF to temperatures of about 200 degree Celsius for about 1 hour. In some implementations, the reduction condition is performed about the super critical condition. However, it should be noted that different implementations may use different pressures, different temperature and/or different time periods.

Figure 11:
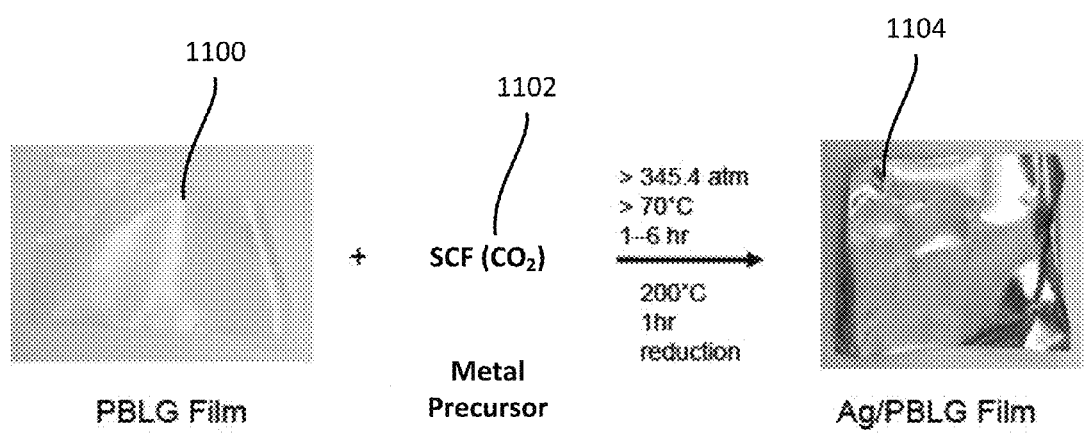
FIG. 11 illustrates a conceptual representation of a method/process of using super critical fluid (SCF) infusion to manufacture a doped chiral polymer metamaterial.

FIG. 11 illustrates another conceptual representation of the process manufacturing a composite material in some implementations. As shown in FIG. 11, a host material 1100 (e.g., chiral polymer film) and a metal (Ag) precursor in a SCF 1102 ($CO_2$) are provided and baked under particular conditions to generate a composite material 1104.

Having described a method for providing/manufacturing a composite material using a super critical fluid process, another method/process for manufacturing providing a composite material will now be provided.

Figure 12:
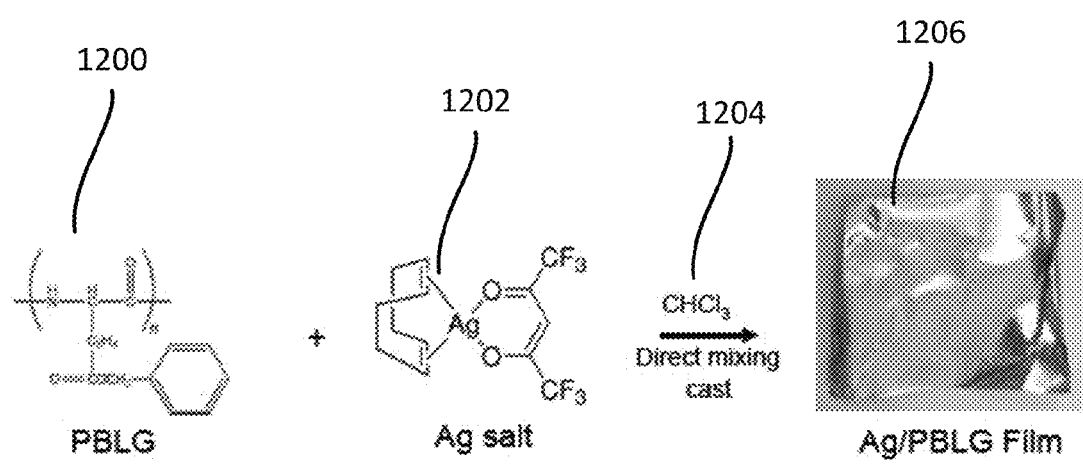
FIG. 12 illustrates another conceptual representation of a direct mixing method/process for manufacturing a composite material that includes a chiral component (PBLG) with a plasmonic nanoinclusion (Ag) precursor.

FIG. 12 illustrates another conceptual representation of a direct mixing method/process for manufacturing a composite material that includes a chiral component. As shown in FIG. 12, a host material 1200 (e.g., chiral polymer) and a silver salt (Ag salt) 1202 are provided in a solution 1204 that includes chloroform ($CHCl_3$) to provide/generate/manufacture a composite material 1206. In some implementations, the host material 1200, the silver salt 1202 and the solution 1104 are in a direct mixing cast. In some implementations, the composite material 1206 is a film composite material.

FIGS. 3-9 illustrate and describe various examples of composite materials that are provided/manufactured based on using one of the above mentioned methods and/or processes.

Figure 13:
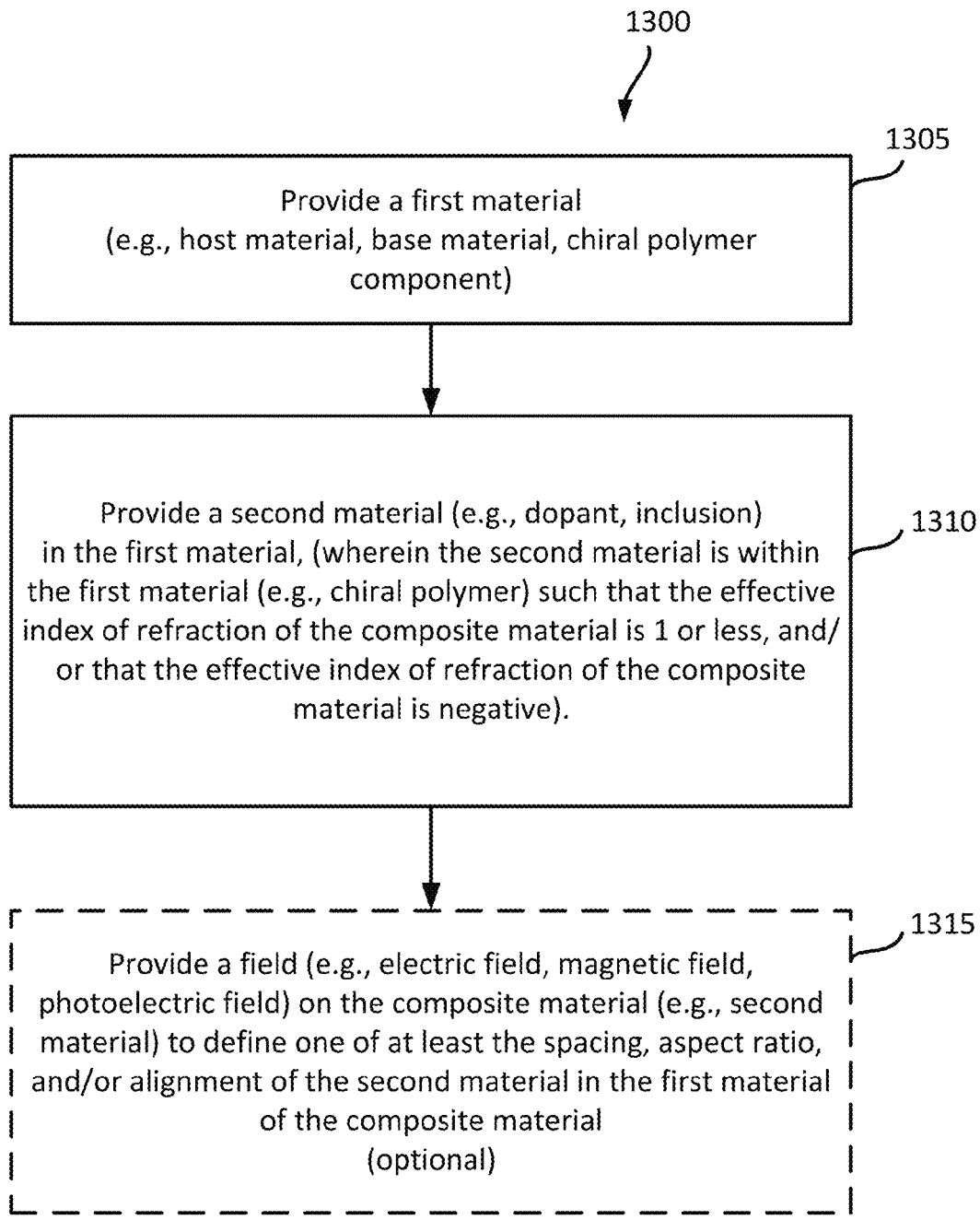
FIG. 13 illustrates a method for providing/manufacturing a composite material.

FIG. 13 illustrates an example of a method for providing/manufacturing a composite material in some implementations. In some implementations, the method of FIG. 13 is a high-level conceptual representation of the methods of FIGS. 10-12 (e.g., super critical fluid method and direct mixing method).

In some implementations, the composite material that is provided/manufactured in FIG. 13 has a negative permittivity (e.g., negative permittivity value), a positive permeability (e.g., positive permeability value), and a negative index of refraction. In some implementations, the composite material that is provided/manufactured is a negative index material (NIM). In some implementations, the composite material that is provided/manufactured has an effective index of refraction that is 1 or less. In some implementations, the composite material has an effective index of refraction that is negative.

As shown in FIG. 13, the method provides (at 1305) a first material. In some implementations, the first material is a host material and/or base material. Different implementations may provide different first materials. In some implementations, the first material includes a chiral component (e.g., chiral polymer, chiral component film). In some implementations, the first material includes one of at least a crystalline chiral helical polymer, poly-γ-benzyl-L-glutamate (PBLG), poly-L-lactic acid (PLA), polypeptide, and/or polyacetylene. In some implementations, the crystalline chiral helical polymer is an aligned liquid crystalline chiral helical polymer.

The method provides (at 1310) a second material in the first material. Different implementations may provide different materials for the second material. In some implementations, the second material includes a dopant. In some implementations, the dopant includes one of at least phosphoric acid ($H_3PO_4$), sulfuric acid ($H_2SO_4$), triflic acid ($CF_3SO_3H$), imidazole ($C_3H_4N_2$), lithium perchlorate ($LiClO_4$), ammonium perchlorate ($NH_4ClO_4$), and/or lithium iodine (LiI).

In some implementations, the second material includes an inclusion. In some implementations, the inclusion includes one of at least plasmonic, nanotubes and/or nanowires. In some implementations, the plasmonic is one of at least silver (Ag) and/or gold (Au). Examples of nanotubes include carbon nanotubes (CNT), boron nitride nanotubes (BNNT), and/or boron carbide nitride nanotubes (BCNNT).

In some implementations, providing (at 1310) the second material in the first material includes dipping and mixing the second material in a liquid solution (e.g., chloroform) that includes the first material. In some implementations, providing (at 1310) the second material in the first material includes infusing the second material in the first material.

In some implementations, the second material is provided within the first material such that the composite material has an effective index of refraction that is 1 or less. In some implementations, the second material is provided within the first material such that the composite material has an effective index of refraction that is negative.

In some implementations, the desired effective index of refraction for the composite material can be achieved by selecting a second material (e.g., dopant, inclusion) with a particular length, spacing, aspect ratio, and alignment. In some implementations, the desired effective index of refraction for the composite material can be achieved by selecting a particular amount of second material to achieve a particular concentration of the second material in the first material and/or composite material.

In some implementations, to specify and/or define the spacing, aspect ratio, and/or alignment of the second material in the first material and/or composite material, an external field (e.g., electric, magnetic, photoelectric) may be optionally provided/applied (at 1315) on the second material, first material and/or the composite material. A method for providing a field on the second material is further described below.

Figure 14:
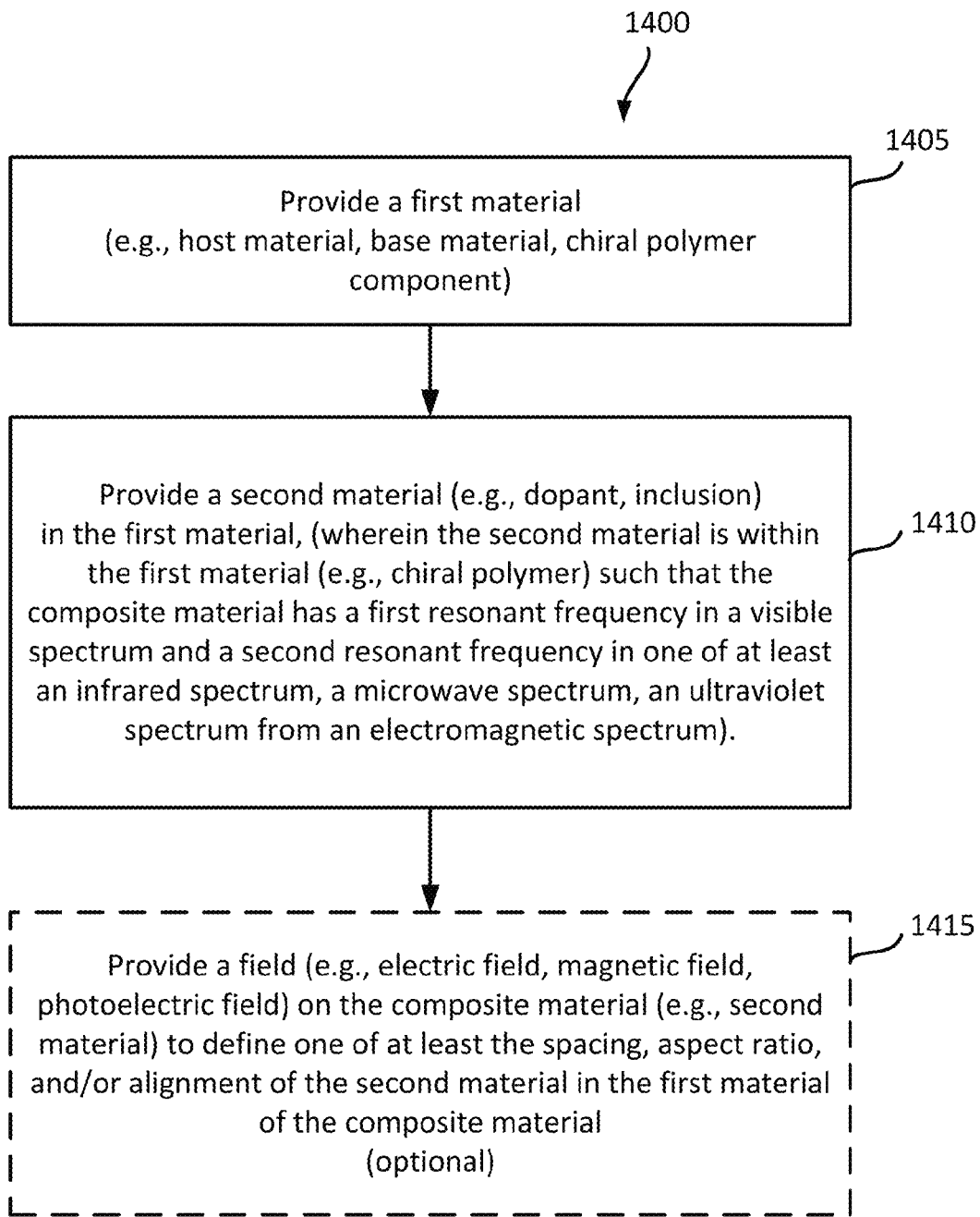
FIG. 14 illustrates a method for providing/manufacturing a composite material.

FIG. 14 illustrates another example of a method for providing/manufacturing a composite material in some implementations. In some implementations, the method of FIG. 14 is a high-level conceptual representation of the methods of FIGS. 10-12 (e.g., super critical fluid method and direct mixing method).

In some implementations, the composite material that is provided/manufactured in FIG. 14 has a negative permittivity (e.g., negative permittivity value), a positive permeability (e.g., positive permeability value), and a negative index of refraction. In some implementations, the composite material that is provided/manufactured is a negative index material (NIM). In some implementations, the composite material that is provided/manufactured has an effective index of refraction that is 1 or less. In some implementations, the composite material has an effective index of refraction that is negative.

As shown in FIG. 14, the method provides (at 1405) a first material. In some implementations, the first material is a host material and/or base material. Different implementations may provide different first materials. In some implementations, the first material includes a chiral component (e.g., chiral polymer, chiral component film). In some implementations, the first material includes one of at least a crystalline chiral helical polymer, poly-γ-benzyl-L-glutamate (PBLG), poly-L-lactic acid (PLA), polypeptide, and/or polyacetylene. In some implementations, the crystalline chiral helical polymer is an aligned liquid crystalline chiral helical polymer.

The method provides (at 1410) a second material in the first material. Different implementations may provide different materials for the second material. In some implementations, the second material includes a dopant. In some implementations, the dopant includes one of at least phosphoric acid ($H_3PO_4$), sulfuric acid ($H_2SO_4$), triflic acid ($CF_3SO_3H$), imidazole ($C_3H_4N_2$), lithium perchlorate ($LiClO_4$), ammonium perchlorate ($NH_4ClO_4$), and/or lithium iodine (LiI).

In some implementations, the second material includes an inclusion. In some implementations, the inclusion includes one of at least plasmonic, nanotubes and/or nanowires. In some implementations, the plasmonic is one of at least silver (Ag) and/or gold (Au). Examples of nanotubes include carbon nanotubes (CNT), boron nitride nanotubes (BNNT), and/or boron carbide nitride nanotubes (BCNNT).

In some implementations, providing (at 1410) the second material in the first material includes dipping and mixing the second material in a liquid solution (e.g., chloroform) that includes the first material. In some implementations, providing (at 1410) the second material in the first material includes infusing the second material in the first material.

In some implementations, the second material is provided within the first material (e.g., chiral polymer) such that the composite material has several resonant frequencies across a visible spectrum and one of at least an infrared spectrum, a microwave spectrum, an ultraviolet spectrum from an electromagnetic spectrum. For example, the second material may be provided in the first material such that the composite material has a first resonant frequency in a visible spectrum and a second resonant frequency in one of at least an infrared spectrum, a microwave spectrum, and/or an ultraviolet spectrum from an electromagnetic spectrum.

In some implementations, the desired resonant frequencies for the composite material can be achieve by selecting a second material (e.g., dopant, inclusion) with a particular length, spacing, aspect ratio, and alignment. In some implementations, the desired resonant frequencies for the composite material can be achieve by selecting a particular amount of second material to achieve a particular concentration of the second material in the first material and/or composite material.

In some implementations, the second material is provided within the first material such that the composite material has an effective index of refraction that is 1 or less. In some implementations, the second material is provided within the first material such that the composite material has an effective index of refraction that is negative.

In some implementations, to specify and/or define the spacing, aspect ratio, and/or alignment of the second material in the first material and/or composite material, an external field (e.g., electric, magnetic, photoelectric) may be optionally provided/applied (at 1415) on the second material, first material and/or the composite material.

It should be noted that the method of FIGS. 13 and 14 are not mutually exclusive. In some implementations, the composite material may be configured to have an effective index of refraction that is 1 or less, a negative index of refraction, and/or several resonant frequencies across several different spectrum of the electromagnetic spectrum.

Figure 15:
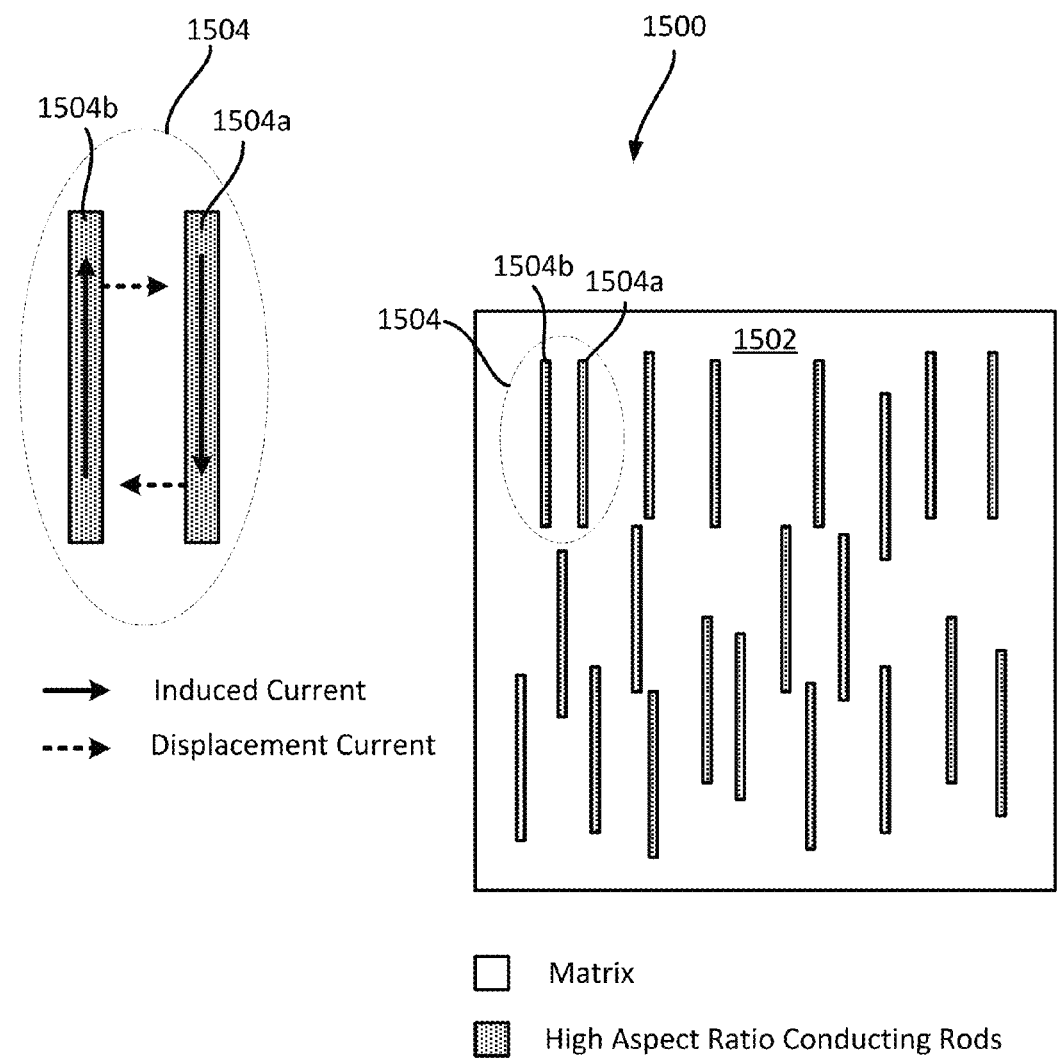
FIG. 15 illustrates a schematic of aligned conductive inclusions in a low dielectric medium, which can generate negative index of refraction under high frequency electromagnetic radiation.

FIG. 15 illustrates how an external field stimuli (e.g., external field) may specify and/or define the spacing, aspect ratio, and/or alignment of the second materials in the first material and/or composite material in some implementations. As shown in FIG. 15, a composite material 1500 includes a first material 1502 and a second material 1504 (e.g., 1504a-1504b). The first material is a chiral polymer material. In some implementations, the chiral material has a permittivity that is about 1

FIG. 15 illustrates that the second material 1504 includes several inclusions (e.g., first inclusion 1504a, second inclusion 1504b). In some implementations, the inclusions are nanoinclusions (e.g., nanotubes, nanowires, nanorods). In some implementations, when the first inclusion 1504a and the second inclusion 1504b are under a high frequency external magnetic field (e.g., electromagnetic radiation), the aligned first and second inclusions 1504a-1504b have an antenna effect and currents are inducted (e.g., excited) in the first and second inclusions 1504a-1504b. In addition, displacement currents are created in the first material 1502 (e.g., chiral component) which lead to the closing of the circuits between the first and second inclusions 1504a-1504b. The displacement currents also generate a local magnetic field. In some implementations, when taking into account the local magnetic field, the resultant effective permeability of the composite material 1500 is negative at frequencies that may depend on the aspect ratio and spacing (e.g., separation) of the conducting first and second inclusions 1504a-1504b. In some implementations, the external stimuli (e.g., external field, electric field, magnetic field, photoelectric effect) is applied during the manufacturing of the composite material. In some implementations, the external stimuli (e.g., external field, electric field, magnetic field, photoelectric effect) is applied after the manufacturing of the composite material.

Configurable Composite Material

FIGS. 16A-16B may also illustrate a composite material that may be tuned to have a different indices of refraction. FIG. 16A illustrates a composite material 1600 that includes a chiral component 1602 (e.g., chiral polymer component) and inclusions 1604. As shown in FIG. 16A, the inclusions 1604 are orientated in a variety and/or random direction. The composite material 1600 may be any of the composite material in the present disclosure. In FIG. 16A, the composite material 1600 is not subject to an external stimuli (e.g., external field, electric field, magnetic field, photoelectric effect) has a first index of refraction (e.g., for a particular wavelength, for a particular frequency).

FIG. 16B illustrates the composite material 1600 under an external stimuli (e.g., external field, electric field, magnetic field, photoelectric effect). As shown in FIG. 16B, the inclusions 1604 are subject to the external stimuli (e.g., external field, electric field, magnetic field, photoelectric effect), which causes the orientation of the inclusions 1614 to be oriented roughly in a particular direction (e.g., approximately horizontal). In some implementations, the inclusions 1604 are aligned with the first material 1602. That is, in some implementations, the inclusions 1604 are aligned with the chiral helical polymers.

In some implementations, when the inclusions 1604 are oriented in a particular direction (e.g., aligned with chiral helical polymers), the composite material 1600 may have particular indices of refraction. In some implementations, when the composite material 1600 is subject to an external stimuli, the composite material 1600 may have a second index of refraction (e.g., for the particular wavelength, for a particular frequency) that is different than the first index of refraction. In some implementations, the strength (e.g., magnitude) and direction of the external stimuli will affect the degree of the alignment of the inclusions, which will affect the index of refraction of the composite material.

In some implementations, the composite material includes a first material (e.g., chiral polymer) and a second material (e.g., nano-inclusion). The composite material is configurable to have a first index of refraction when the second material is under a first external stimuli. The composite material is configurable to have a second index of refraction when the composite material is under a second external stimuli. In some implementations, the first external stimuli is a zero external stimuli (e.g., no external stimuli).

In some implementations, the particular frequency is in one of at least a visible spectrum, an infrared spectrum, a microwave spectrum, and/or an ultraviolet spectrum. In some implementations, the particular wavelength is in one of at least a visible spectrum, an infrared spectrum, a microwave spectrum, and/or an ultraviolet spectrum.

In some implementations, FIGS. 16A-16B may also illustrate a composite material that may be tuned to have a different resonant frequency, since changing the index of refraction of the composite material may affect the resonant frequency of the composite material. FIG. 16A illustrates a composite material 1600 that includes a chiral component 1602 (e.g., chiral polymer component) and inclusions 1604.

As shown in FIG. 16A, the inclusions 1604 are orientated in a variety and/or random direction. The composite material 1600 may be any of the composite material in the present disclosure. In FIG. 16A, the composite material 1600 is not subject to an external field (e.g., electric, magnetic field) has a first resonant frequency.

FIG. 16B illustrates the composite material 1600 under an external field (e.g., electric, magnetic field). As shown in FIG. 16B, the inclusions 1604 are subject to the external field (e.g., magnetic field), which causes the orientation of the inclusions 1614 to be oriented roughly in a particular direction (e.g., approximately horizontal). In some implementations, when the inclusions 1614 are oriented in a particular direction, the composite material 1610 may have particular resonant frequencies across different spectrum of the electromagnetic spectrum. In some implementations, when the composite material 1600 is subject to an external field, the composite material 1600 may have a second resonant frequency that is different than the first resonant frequency. In some implementations, the strength (e.g., magnitude) and direction of the external field will affect the degree of the alignment of the inclusions, which will affect the resonant frequency of the composite material.

Alignment/Drawing Out/Stretching of Composite Material

FIG. 17 illustrates an example of a method for providing/manufacturing a composite material in some implementations. In some implementations, the composite material that is provided/manufactured in FIG. 17 has a positive or negative permittivity (e.g., negative permittivity value), a positive or negative permeability (e.g., positive permeability value), and a negative index of refraction (or an index of refraction that is 1 or less). In some implementations, the composite material that is provided/manufactured is a negative index material (NIM). In some implementations, the composite material that is provided/manufactured has an effective index of refraction that is 1 or less. In some implementations, the composite material has an effective index of refraction that is negative.

As shown in FIG. 17, the method provides (at 1705) a first material. In some implementations, the first material is a host material and/or base material. Different implementations may provide different first materials. In some implementations, the first material includes a chiral component (e.g., chiral polymer, chiral film). In some implementations, the first material includes one of at least a crystalline chiral helical polymer, poly-γ-benzyl-L-glutamate (PBLG), poly-L-lactic acid (PLA), polypeptide, and/or polyacetylene. In some implementations, the crystalline chiral helical polymer is an aligned liquid crystalline chiral helical polymer.

The method provides (at 1710) a second material in the first material. Different implementations may provide different materials for the second material. In some implementations, the second material includes a dopant. In some implementations, the dopant includes one of at least phosphoric acid ($H_3PO_4$), sulfuric acid ($H_2SO_4$), triflic acid ($CF_3SO_3H$), imidazole ($C_3H_4N_2$), lithium perchlorate ($LiClO_4$), ammonium perchlorate ($NH_4ClO_4$), and/or lithium iodine (LiI).

In some implementations, the second material includes an inclusion. In some implementations, the inclusion includes one of at least plasmonic, nanotubes and/or nanowires. In some implementations, the plasmonic is one of at least silver (Ag) and/or gold (Au). Examples of nanotubes include carbon nanotubes (CNT), boron nitride nanotubes (BNNT), and/or boron carbide nitride nanotubes (BCNNT).

In some implementations, providing (at 1710) the second material in the first material includes dipping and mixing the second material in a liquid solution (e.g., chloroform) that includes the first material. In some implementations, providing (at 1710) the second material in the first material includes infusing the second material in the first material.

In some implementations, the second material is provided within the first material such that the composite material has an effective index of refraction that is 1 or less. In some implementations, the second material is provided within the first material such that the composite material has an effective index of refraction that is negative.

In some implementations, the desired effective index of refraction for the composite material can be achieved by selecting a second material (e.g., dopant, inclusion) with a particular length, spacing, aspect ratio, and alignment. In some implementations, the desired effective index of refraction for the composite material can be achieved by selecting a particular amount of second material to achieve a particular concentration of the second material in the first material and/or composite material.

In some implementations, the method may optionally provide (at 1715) an alignment of the composite material. In some implementations, providing an alignment includes drawing out (e.g., stretching out) the first material. A method for providing an alignment of the composite material (e.g., the first material) is further described below.

FIG. 18 illustrates a conceptual representation of a method/process for drawing out a composite material that includes a chiral component. As shown in FIG. 18, an undrawn composite material 1800 is heated to a temperature of greater than 70 degrees Celsius. In some implementations, the undrawn composite material 1800 is a composite material manufactured using one of the methods described in FIGS. 13-14 (e.g., super critical fluid method, direct mixing method). The undrawn composite material 1800 is then soaked for at least 30 minutes (e.g., baked in set temperature for a set amount of time). Next, the undrawn composite material 1800 is drawn (e.g., stretched). Different implementations may use different processes for drawing/stretching the undrawn composite material 1800. Next, the drawn composite material 1802 is cooled to room temperate in some implementations. In some implementations, stretching the composite materials aligns the first material (e.g., chiral polymer) in the direction of the stretching. In some implementations, stretching, drawing, aligning the composite material along a direction decrease the permittivity of the composite material. In some implementations, decreasing the permittivity of the composite material may provide the composite material with an index of refraction that is 1 or less, and/or a negative index of refraction.

FIG. 19 illustrates a scanning electron micrograph (SEM) illustration of a drawn out composite material 1900 in some implementations. As shown in FIG. 19, the composite material 1900 is stretched out vertically. In some implementations, the composite material 1900 may be stretched out in a different direction (e.g., horizontally).

FIGS. 20-23 illustrate various scanning electron micrographs (SEM) illustrations of composite materials. In some figures, the composite materials are undrawn. In other figures, the composite materials are drawn out (e.g., stretched). FIG. 20 illustrates an undrawn composite material. FIGS. 21-23 illustrates drawn composite materials.

Exemplary Properties Values of Composite Material Comprising Chiral Material

As described above the composite material (e.g., composite material 200) in the present disclosure is an electromagnetic material with unique and/or exotic electromagnetic properties. FIGS. 24-27 illustrates various exemplary material properties values for one or more different types of composite materials that includes a chiral component (e.g., chiral polymer component).

FIG. 24 illustrates the permittivity of various composite materials along different frequencies. As shown in FIG. 24, the addition of an inclusion (e.g., silver (Ag)) decreases the permittivity of the composite materials at high frequencies. FIG. 24 also illustrates that the drawing out (e.g., stretching) of the composite materials decreases the permittivity of the composite materials.

FIG. 25 illustrates the loss permittivity of various composite materials along different frequencies. As shown in FIG. 25, super critical fluid process or the alignment did not increase the loss factor.

FIGS. 26 and 27 illustrates the index of refraction of various composite materials along different wavelengths. As shown in FIG. 27, the addition of an inclusion (e.g., silver (Ag)) decreases the effective index of refraction to 1 or less at a resonance frequency. FIG. 28 illustrates that the drawing out (e.g., stretching) of the composite materials also further decrease the effective index of refraction to 1 or less.

Exemplary Devices Comprising Composite Material

The composite materials (e.g., composite materials 200, 1500) described in the present application may be used in variety of applications and devices. In some implementations, the composite materials may be incorporated in devices configured for beam steering, miniature solid state filters, ultra-thin backwards antennas, super lenses, optical limiters, a supersensitive sensor, and/or cloaking device.

One or more of the elements, steps, features, and/or functions illustrated in FIGS. 2, 3, 4, 5, 6, 7, 8, 9, 10, 11, 12, 13, 14, 15, 16A-16B, 17, 18, 19, 20, 21, 22, 23, 24, 25, 26, and/or 27 may be rearranged and/or combined into a single component, step, feature or function or embodied in several components, steps, or functions. Additional elements, components, steps, and/or functions may also be added without departing from the invention.

The word "exemplary" is used herein to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other.

The term "spectrum" as used herein may include the entire spectrum or a region of the entire spectrum. For example, a visible spectrum may include the entire visible spectrum or a portion and/or a region of the entire spectrum.

The various features of the invention described herein can be implemented in different systems without departing from the invention. It should be noted that the foregoing aspects of the disclosure are merely examples and are not to be construed as limiting the invention. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

What is claimed is:

1. A composite material comprising:
a first material comprising a chiral polymer; and
a second material within the chiral polymer, wherein the first material and the second material are configured to provide an effective index of refraction value for the composite material of 1 or less;
wherein the composite material has zero or greater permittivity value.

2. The composite material of claim 1, wherein the effective index of refraction value for the composite material is negative.

3. The composite material of claim 1, wherein the effective index of refraction value for the composite material of 1 or less is at least in a wavelength of one of at least a visible spectrum, an infrared spectrum, a microwave spectrum, and/or an ultraviolet spectrum.

4. The composite material of claim 1, wherein the composite material has a negative permittivity value.

5. The composite material of claim 1, wherein the second material is a plasmonic inclusion.

6. The composite material of claim 1, wherein the composite material has a negative permeability value.

7. The composite material of claim 1, wherein the composite material has zero or greater permeability value.

8. The composite material of claim 1, wherein the effective index of refraction value for the composite material is based on at least a chiral parameter of the composite material.

9. The composite material of claim 1, wherein the first material has a first chiral parameter and the composite material comprising the first and second materials has an overall second chiral parameter, wherein the second material is configured to cause the second chiral parameter of the composite material to be greater than the first chiral parameter of the first material.

10. The composite material of claim 1, wherein the chiral polymer includes one of at least a crystalline chiral helical polymer, poly-y-benzyl-L-glutamate (PBLG), poly-L-lactic acid (PLA), polypeptide, and/or polyacetylene.

11. The composite material of claim 1, wherein the second material is one of at least a dopant and/or an inclusion.

12. The composite material of claim 1, wherein the second material is one of at least ionic dopant, phosphoric acid ($H_3PO_4$), sulfuric acid ($H_2SO_4$) triflic acid ($CF_3SO_3H$), imidazole ($C_3H_4N_2$), lithium perchlorate ($LiClO_4$), ammonium perchlorate ($NH_4ClO_4$), and/or lithium iodine (LiI).

13. The composite material of claim 1, wherein the second material is one of at least nanoparticles, nanotuhes, nanoplatelets, and/or nanowires.

14. The composite material of claim 13, wherein the nanotube is one of at least a carbon nanotuhe (CNT), a boron nitride nanotube (BNNT), and/or a boron carbide nitride nanotube (BCNNT).

15. The composite material of claim 1, wherein the second material is a plasmonic inclusion comprising one of at least silver (Ag) and/or gold (Au).

16. The composite material of claim 1, wherein the first material is aligned along a particular direction.

17. The composite material of claim 1, wherein the second material is aligned along a particular direction in the first material.

18. The composite material of claim 17, wherein the second material being aligned along the particular direction causes the composite material to have a greater chiral parameter.

19. The composite material of claim 1, wherein the composite material is stretched along a particular direction.

20. The composite material of claim 19, wherein the composite material being stretched along the particular direction causes the composite material to have a greater chiral parameter.

21. The composite material of claim 1, wherein the composite material is configured to be incorporated in one of at least a device configured for beam steering, a miniature solid state filter, an ultra-thin backwards antenna, a super lens, an optical limiter, a supersensitive sensor, and/or a cloaking device.

22. A composite material comprising:
a first material comprising a chiral polymer; and
a second material within the chiral polymer, wherein the second material is within the chiral polymer such that the composite material has a first resonant frequency in a visible spectrum and a second resonant frequency in one of at least an infrared spectrum, a microwave spectrum, and/or an ultraviolet spectrum from an electromagnetic spectrum;
wherein the first material and the second material are configured to provide an effective index of refraction value for the composite material of 1 or less, and wherein the composite material has zero or greater permittivity value.

23. The composite material of claim 22, wherein the composite material has an effective index of refraction value of 1 or less.

24. The composite material of claim 22, wherein the composite material has a negative effective index of refraction value.

25. The composite material of claim 22, wherein the composite material has a negative permittivity value.

26. The composite material of claim 22, wherein the second material is a plasmonic inclusion.

27. The composite material of claim 22, wherein the composite material has a negative permeability value.

28. The composite material of claim 22, wherein the composite material has zero or a positive permeability value.

29. The composite material of claim 22, wherein the first material has a first chiral parameter and the composite material comprising the first and second materials has an overall second chiral parameter, wherein the second material is configured to cause the second chiral parameter of the composite material to be greater than the first chiral parameter of the first material.

30. The composite material of claim 22, wherein the chiral polymer includes one of at least a crystalline chiral helical polymer, poly-y-benzyl-L-glutamate (PBL G), poly-L- lactic acid (PLA), polypeptide, and/or polyacetylene.

31. The composite material of claim 22, wherein the second material is one of at least a depart and/or an inclusion.

32. The composite material of claim 22, wherein the second material is one of at least ionic dopant, phosphoric acid ($H_3PO_4$), sulfuric acid ($H_2 SO_4$), triflic acid ($CF_3SO_3H$), imidazole ($C_3H_4N_2$), lithium perchlorate ($LiClO_4$), ammonium perchlorate ($NH_4ClO_4$), and/or lithium iodine (LiI).

33. The composite material of claim 22, wherein the second material is one of at least nanoparticles, nanotubes, nanopiatelets, and/or nanowires.

34. The composite material of claim 33, wherein the nanotube is one of at least a carbon nanotube (CNT), a boron nitride nanotube (BNNT), and/or a boron carbide nitride nanotube (BCNNT).

35. The composite material of claim 22, wherein the second material is a plasmonic inclusion comprising one of at least silver (Ag) and/or gold (Au).

36. The composite material of claim 22, wherein the second material is aligned along a particular direction. in the first material, wherein the second material being aligned along the particular direction causes the composite material to have a greater chiral parameter.

37. The composite material of claim 22, wherein the composite material is stretched along a particular direction, wherein the composite material being stretched along the particular direction causes the composite material to have a greater chiral parameter.

38. The composite material of claim 22, wherein the composite material is configured to be incorporated in one of at least a device configured for beam steering, a miniature solid state filter, an ultra-thin backwards antenna, a super lens, an optical limiter, a supersensitive sensor, and/or a cloaking device.

39. A composite material comprising:
a first material comprising a chiral polymer; and
a second material within the chiral polymer, wherein the composite material is configurable to have a first index of refraction when the second material is under a first external stimuli and a second index of refraction when the second material is under a second external stimuli, wherein the first material and the second material are configured such that the first index of refraction has a value of 1 or less, and wherein the composite material has zero or greater permittivity value.

40. The composite material of claim 39, wherein the first external stimuli is a zero external field.

41. The composite material of claim 39, wherein the first and second external stimulus are one of at least an electric field, a magnetic field, and/or photoelectric effect.

42. The composite material of claim 39, wherein the first index of refraction is the first index of refraction at a first frequency, and the second index of refraction is the second index of refraction at the first frequency.

* * * * *